United States Patent [19]

Abraham et al.

[11] 4,007,171
[45] Feb. 8, 1977

[54] INTERMEDIATES FOR PROSTANOIC ACIDS

[75] Inventors: Nedumparambil A. Abraham, Dollard des Ormeaux; Jehan F. Bagli, Kirkland; Tibor Bogri, Montreal, all of Canada

[73] Assignee: American Home Products Corporation, New York, N.Y.

[22] Filed: Apr. 10, 1975

[21] Appl. No.: 567,036

Related U.S. Application Data

[62] Division of Ser. No. 351,381, April 16, 1973, Pat. No. 3,917,668.

[52] U.S. Cl. .................. 260/240 R; 260/448.8 R; 260/468 H
[51] Int. Cl.$^2$ ........................................ C07C 69/74
[58] Field of Search ....... 260/468 H, 468 D, 240 R, 260/448.8 R

[56] References Cited
OTHER PUBLICATIONS

Abraham, Tet. Letters, 451 (1973).

*Primary Examiner*—Robert Gerstl

[57] ABSTRACT

15- And/or 16-alkyl derivatives of 9,15-dioxygenated prost-13-enoic, prosta-4,13-dienoic and prosta-5,13-dienoic acid, lower alkyl esters thereof and homologs thereof, as well as a process for preparing these derivatives are disclosed. The compounds possess hypotensive, antihypertensive, bronchospasmolytic, gastric acid secretion inhibiting, abortifacient, estrus synchronizing and ovulation regulating properties. The compounds also inhibit the aggregation of platelets and promote the disaggregation of aggregated platelets. Methods for their use are also disclosed.

10 Claims, No Drawings

INTERMEDIATES FOR PROSTANOIC ACIDS

This is a division of application Ser. No. 351,381, filed Apr. 16, 1973 now U.S. Pat. No. 3,917,668.

BACKGROUND OF THE INVENTION

1. Field of Invention

The invention relates to prostaglandin derivatives. More particularly, this invention relates to 9,15-dioxygenated derivatives of prost-13-enoic, prosta-4,13-dienoic and prosta-5,13-dienoic acids having lower alkyl substituents, to homologs thereof, to intermediates used in their preparation and to a process for preparing these compounds.

2. Description of the Prior Art

A prostaglandin (PG) is a naturally occurring C-20 fatty acid. The natural prostaglandin molecule contains a cyclopentane nucleus with two side chains in trans configuration. The fundamental structure is called prostanoic acid and is conventionally represented as follows:

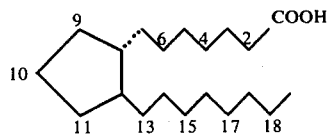

The chemistry and pharmacological effects of the prostaglandins have been the subject of several recent reviews; for example, see E. W. Horton, Physiol. Rev., 49, 122 (1969), J. F. Bagli in "Annual Reports in Medicinal Chemistry, 1969", C. K. Cain, Ed., Academic Press, New York and London, 1970, p. 170, and J. E. Pike in "Progress in the Chemistry of Organic Natural Products", Vol. 28, W. Herz, et al. Eds., Springer Verlag, New York, 1970, p. 313.

The pharmacological effects known to be associated with the prostaglandins relate to the reproductive, cardiovascular, respiratory, gastrointestinal and renal systems.

Due to the increasing interest in these natural products a rather extensive effort has been given recently to the synthesis of prostaglandins and their analogs. Included among these syntheses are several synthetic methods for the preparation of 9,15-dioxygenated derivatives of prostanoic or prost-13-enoic acid. For example, the synthesis of the first pharmacologically active 9,15-dioxygenated prostanoic acid derivative, 9ξ,15ξ-dihydroxyprost-13-enoic acid (11-desoxyprostaglandin F$_1$) was reported in detail by J. F. Bagli, T. Bogri and R. Deghenghi, Tetrahedron Letters, 465 (1966). A significant simplification and modification of that process was described by Bagli and Bogri in U.S. Pat. No. 3,455,992, issued July 15, 1969, whereby 9ξ,15ξ-dihydroxyprost-13-enoic acid as well as homologs thereof were obtained, see also Bagli and Bogri, Tetrahedron Letters, 5 (1967).

Further improvements in the synthesis of 9,15-dioxygenated derivatives of prostanoic acid have been described by Bagli and Bogri in Tetrahedron Letters, 1639 (1969) and German Offenlegungsschrift No. 1,953,232, published Apr. 30, 1970, and in British patent specification No. 1,097,533, published Jan. 3, 1968.

Other recent syntheses of 9,15-dioxygenated derivatives are reported in Belgian Pat. No. 766,521, published Nov. 3, 1971, P. Crabbé and A. Guzman, Tetrahedron Letters, 115 (1972), M. P. L. Caton, et al., Tetrahedron Letters, 773 (1972), C. J. Sih, et al., Tetrahedron Letters, 2435 (1972), F. S. Alverez, et al., J. Amer. Chem. Soc., 94, 7823 (1972), A. F. Kluge, et al., J. Amer. Chem. Soc., 94, 9256 (1972), and N. A. Abraham, Tetrahedron Letters, 451, 1973.

More recently, Bagli and Bogri have extended the scope of their processes for preparing 9,15-dioxygenated derivatives of prostanoic acid to include the preparation of 9-oxo-15-hydroxy prostanoic acid derivatives having an alkyl substituent at position 15, U.S. Pat. No. 3,671,570, issued June 20, 1972. These 15-alkyl derivatives possess hypotensive, antihypertensive, bronchospasmolytic and gastric acid secretion inhibiting properties, as well as inhibiting the aggregation of platelets and promoting the disaggregation of aggregated platelets.

It is noteworthy that the synthetic 9,15-dioxygenated prostanoic acid derivatives described above possess a number of the biological activities of the natural compounds although they lack the 11-hydroxyl of the latter.

In the natural series attention has been focused recently on certain 15-methyl and 16,16dimethyl derivatives.

15-Methyl PGF$_{2\alpha}$ and 15-methyl PGE$_2$ methyl esters have been reported to interrupt pregnancy in the rhesus monkey and in the human, K. T. Kirton et al., Ann. N. Y. Acad. Sci., 180, 445(1971). Furthermore, 15(R)-methyl and 15(S)-methyl PGE$_2$ has been reported to inhibit gastric secretion, see Medical World News, Oct. 20, 1972, p. 70M. Likewise, 16,16-dimethyl PGE$_2$ methyl ester has been described as effective in inhibiting gastric acid secretion, Chemistry, and Engineering News, Oct. 16, 1972, p. 12.

It is worth noting at this point that the natural PGE$_1$, PGE$_2$, PGF$_{1\alpha}$ and PGF$_{2\alpha}$ do have the disadvantage of being relatively unstable, see T. O. Oesterling, et al., J. Pharm. Sci., 61, 1861 (1972). For example, it is well known that the 11hydroxy group of PGE$_1$ and PGE$_2$ participates readily in dehydration reactions under both basic and acidic conditions, see S. Bergstrom et al., J. Biol. Chem. 238, 3555 (1963), E. J. Corey et al., J. Amer. Chem. Soc., 90, 3245 (1968), J. E. Pike et al., J. Org. Chem. 34, 3552 (1969) and "The Prostaglandins, Progress in Research", S. M. M. Karim, Ed., Wiley-Interscience, New York, 1972, p. 10.

As realized by those skilled in the art this inherent disadvantage of the natural compounds must always be taken into account when considering the practical aspects of preparation, formulation of storage of these compounds. In contrast, the compounds of the present invention are free from this disadvantage.

In brief, although 15-alkylated derivatives of both the 9,15-dioxygenated derivatives of prostanoic acids, i.e. 11-deoxyprostaglandins, and the 15- and 16-alkylated derivatives of natural prostaglandins have been described as exhibiting effects on the gastrointestinal system, and although certain methyl esters of the 15-alkylated natural derivatives have been described as having effects on the reproductive system, it would appear that the latter effects have never been associated with 15- and/or 16-alkyl analogs of the 9,15-dioxygenated derivatives.

It is the purpose of the present application to disclose the discovery of certain stable 15-alkylated and/or 16-alkylated derivatives of the 9,15-dioxygenated derivatives of prostanoic acid having unexpected high activity regarding effects on the reproductive system. More specifically, the compounds of this invention are effective agents for inducing abortion and for synchronization of estrus and regulation of ovulation in animals.

SUMMARY OF THE INVENTION

The compounds prepared by the process of this invention are represented by formula 1:

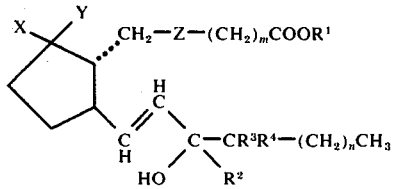

in which $m$ is an integer from zero to two, $n$ is an integer from two to five, X and Y together represent oxo, or X represents, hydroxy and Y is hydrogen, Z represents the radical $-(CH_2)_3-$, cis$-CH=CH-CH_2-$ or cis$-CH_2-CH=CH-$, $R^1$ is hydrogen or lower alkyl and $R^2$, $R^3$ and $R^4$ each are hydrogen or lower alkyl with the provisos that at least one of $R^2$, $R^3$ or $R^4$ is lower alkyl and at least one of $R^2$, $R^3$ or $R^4$ is hydrogen.

Among the preferred compounds of this invention are the compounds of formula 1 in which $m$ is the integer two and $n$ is the integer three.

The compounds of formula 1 are prepared by a process in which the starting material is the aldehyde of formula L—CHO (2) in which L is the radical A, B or C:

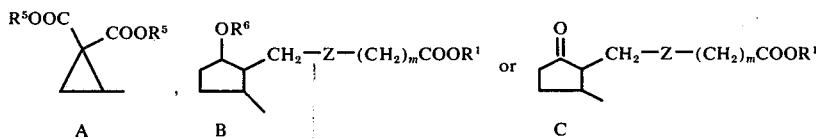

wherein $R^1$ and $R^5$ each are lower alkyl, $R^6$ is a radical suitable for protecting a hydroxy group and Z and $m$ are as defined hereinbefore.

Depending on the nature of L of the aldehyde of formula L—CHO, the process of this invention is elaborated in the following manner:

In the case where L of the aldehyde of formula L—CHO is radical A, the aldehyde is treated with a Wittig reagent of the formula $(AlkO)_2POCH_2COCR^3R^4-(CH_2)_nCH_3$ in which Alk is an alkyl containing one to three carbon atoms and $R^3$, $R^4$ and $n$ are as defined hereinbefore to obtain the corresponding compound of formula 3

$$L-CH=CHCOCR^3R^4-(CH_2)_nCH_3 \qquad (3)$$

in which L, $R^3$, $R^4$ and $n$ are as defined hereinbefore; the last-named compound of formula 3 is then treated with a metal borohydride or a lower alkyl magensium halide to give the corresponding compound of formula 4

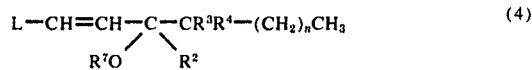

in which L is the radical A as defined herein, $R^3$, $R^4$ and $n$ are as defined herein, $R^7$ is hydrogen and $R^2$ is respectively hydrogen or lower alkyl; optionally followed by treating the compound of formula 4, so obtained, with a reagent known to be effective for converting a hydroxy group of known compounds to a protected hydroxy group, to obtain the corresponding compound of formula 4 in which L is the said radical A, $R^2$, $R^3$, $R^4$ and $n$ are as defined herein and $R^7$ is a radical suitable for protecting a hydroxy group.

Thereafter, the instant compound of formula 4 is treated with a malonic ester derivative of formula 5

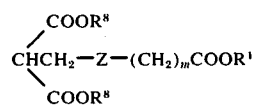

in which $R^1$ and $R^8$ each are lower alkyl and Z and $m$ are as defined herein, in the presence of a base whereby the compounds of formulae 4 and 5 undergo a base catalyzed condensation to give the corresponding cyclopentanonetriester of formula 6,

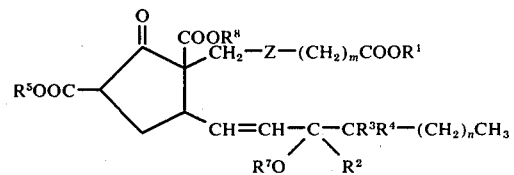

in which $m$, $n$, Z, $R^2$, $R^3$, $R^4$, $R^5$ and $R^8$ are as defined hereinbefore, $R^1$ is lower alkyl and $R^7$ is hydrogen or a radical suitable for protecting a hydroxy group; followed, when $R^7$ is a radical suitable for protecting a hydroxy group, by treating the last-named cyclopentanonetriester of formula 6 with an agent known to be effective for removing said protecting group to obtain the corresponding compound of formula 6 in which $R^7$ is hydrogen.

The instant compound of formula 6 is now treated with a base in the presence of water to give the corresponding keto compound of formula 1 in which $m$, $m$, Z, $R^2$, $R^3$ and $R^4$, are as defined herein, X and Y together are oxo and $R^1$ is hydrogen: thereafter, and if desired, the last-named compound is treated with a lower alkanol containing one to three carbon atoms in the presence of an acid catalyst to obtain the corresponding ester derivative of formula 1 in which $m$, $n$, Z, $R^2$, $R^3$ and $R^4$ are as defined herein, X and Y together are oxo and $R^1$ is lower alkyl.

Alternatively, in the case where L of the aldehyde of formula L—CHO is radical B, the aldehyde is treated with the above Wittig reagent of formula $(AlkO)_2$-$POCH_2COCR^3R^4$—$(CH_2)_nCH_3$ in which Alk is an alkyl containing one to three carbon atoms and $R^3$, $R^4$ and $n$ are as defined hereinbefore, to obtain the corresponding compound of formula 3, noted above, in which L is the radical B as defined hereinbefore and $R^3$, $R^4$ and $n$ are as defined hereinbefore.

Thereafter the compound of formula 3 is treated with either a metal borohydride or a lower alkyl magnesium halide to give the corresponding compound of formula 4, as noted above, in which L is the radical B as defined herein, $R^3$, $R^4$ and $n$ are as defined herein, $R^7$ is hydrogen and $R^2$ is respectively hydrogen or lower alkyl, followed by subjecting the latter compound to conditions known to be effective for removing the radical suitable for protecting a hydroxy group of known compounds, to give the corresponding compound of formula 1 in which $m$, $n$, Z, $R^2$, $R^3$ and $R^4$ are as defined herein, X is hydroxy, Y is hydrogen and $R^1$ is lower alkyl.

Thereafter, and if desired, the last-named compound of formula 1 in which $R^2$ is lower alkyl is treated with an oxidizing agent to afford the corresponding keto compound of formula 1 in which $m$, $n$, Z, $R^3$ and $R^4$ are as defined hereinbefore, $R^1$ and $R^2$ are lower alkyl and X and Y together are oxo.

Again alternatively, in the case where L of the aldehyde of formula L—CHO is radical C, the aldehyde is treated with a Wittig reagent of the formula $(AlkO)_2$-$POCH_2COCR^3R^4$—$(CH_2)_nCH_3$ in which Alk is an alkyl containing one to three carbon atoms, $R^3$ and $R^4$ each are hydrogen or lower alkyl with the proviso that at least one of $R^3$ or $R^4$ is lower alkyl and $n$ is as defined hereinbefore, to obtain the corresponding compound of formula 3 noted above, in which L is the radical C as defined hereinbefore and $R^3$, $R^4$ and $n$ are as defined hereinbefore.

Thereafter, the instant keto compound of formula 3 is converted to a corresponding ketal derivative, viz., the compound of formula 3 in which L is the radical D:

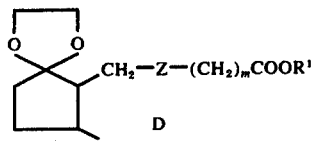

in which Z and $m$ are as defined hereinbefore and $R^1$ is lower alkyl, by treating said keto compound with ethylene glycol in the presence of an acid catalyst.

The ketal derivative of formula 3 is now treated with a metal borohydride to give the corresponding compound of formula 4, noted above, in which L is the said radical D, $R^3$, $R^4$ and $n$ are as defined herein, $R^2$ is hydrogen and $R^7$ is hydrogen; followed by treating said last-named compound with an acid in the presence of water to obtain the corresponding compound of formula 1.

Thereafter, if desired, the aforementioned ester compound of formula 1 in which $R^1$ is lower alkyl, obtained by any of elaborations of the process noted above, is converted to its corresponding free acid, a compound of formula 1 in which $R^1$ is hydrogen, by treatment with a base in the presence of water.

Likewise, if desired, the aforementioned keto compound of formula 1 in which X and Y together are oxo, obtained by any of the elaborations of the process noted above, is treated with a complex borohydride to give the corresponding compound of formula 1 in which X is hydroxy and Y is hydrogen.

DETAILS OF THE INVENTION

The numbering system applied to the compounds of this invention, as used hereinafter, refers to the $\omega$-cyclopentyl(lower)alkanoic acid nucleus.

A feature of this invention is that the process described herein leads to the compounds of formula 1 in which the two side chains are in the trans configuration characteristic for the natural prostaglandins. Also, like the natural prostaglandins a double bond in the acid side chain of the compounds of this invention has the cis configuration and the double bond in the side chain bearing the hydroxy group has the trans configuration.

Notwithstanding the preceding considerations the compounds of this invention having one or more asymmetric carbon atoms can exist in the form of various stereochemical isomers. More specifically, the compounds are produced as a mixture of racemates. These mixtures result from the asymmetric centers bearing a hydroxyl group and can be separated into pure racemates at appropriate stages by methods well known in the art, for example, see below. If desired, the racemates can be resolved into enantiomorphs also by known methods. It is to be understood that such racemates and enantiomorphs are included within the scope of this invention.

Furthermore, it is to be understood that the pictorial representations used herein illustrating the compounds of this invention, are to be construed as including such racemates and enantiomorphs. For example, in formula 1 the dotted line joining the acid side chain to the cyclopentane ring and the solid line joining the side chain bearing the hydroxy group are used for the purpose of illustrating the trans relationship of these two side chains and should not be construed as limiting the compounds to one enantiomorph but rather as including all possible enantiomorphs having this trans relationship.

Also included within this invention are the pharmaceutically acceptable salts of the acids of formula 1 in which $R^1$ is hydrogen. The latter compounds are transformed in excellent yield into the correpsonding pharmaceutically acceptable salts by neutralization of said latter compounds with the appropriate inorganic or organic base. The relative stabilty of the acid facilitates this transformation. The salts possess the same activities as the parent acid compounds when administered to animals and may be utilized in the same manner. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines: lower mono-, di- and trialkylamines, the alkyl radicals of which contain up to 3 carbon atoms, such as methylamine, dimethylamine, trimethylamine, ethylamine, di- and triethylemine, methylethylamine, and the like; mono-, di- and trialkanolamines, the alkanol radicals of which contain up to 3 carbon atoms, such as mono-, di- and triethanolamine; alkylene-diamines which contain up to 6 carbon atoms, such as hexamethylenediamine; cyclic saturated or unsaturated bases containing up to 6 carbon atoms, such as pyrrolidine, piperidine, morpholine, piperazine and their N-alkyl and N-hydroxyalkyl derivatives, such as N-methyl-morpholihne and N-(2-hydroxyethyl)-piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methylpyridinium, N-methyl-N-(2-hydroxyethyl)-pyrrolidinium, N,N-dimethylmorpholinium, N-methyl-N-(2-hydroxyethyl)morpholinium, N,N-dimethylpiperidinium and N-methyl-N-(2-hydroxyethyl)-piperidinium salts, which are characterized by an especially good water-solubility. In principle, however, there can be used all ammonium salts which are physiologically compatible.

The transformations to the salts can be carried out by a variety of methods known in the art. For example, in the case of the inorganic salts, it is preferred to dissolve the selected acid in water containing at least an equivalent amount of a hydroxide, carbonate, or bicarbonate corresponding to the inorganic salt desired. Advantageously, the reaction is performed in an inert organic solvent, for example, methanol, ethanol, dioxane, and the like. For example, such use of sodium hydroxide, sodium carbonate or sodium bicarbonate gives a solution of the sodium salt. Evaporation of the water or addition of a water-miscible solvent of moderate polarity, for example, a lower alkanol or a lower alkanone gives the solid inorganic salt if that form is desired.

To produce an amine salt, the selected acid is dissolved in a suitable solvent of either moderate or lower polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or diethyl ether or by evaporation. If the amine is relatively volatile, any excess can easily be removed by evaporation. It is preferred to use equivalent amounts of the less volatile amines.

Salts wherein the cation is quaternary ammonium are produced by mixing the selected acid with an equivalent amount of the corresponding quaternary ammonium hydroxide in water solution, followed by evaporation of the water.

The term "lower alkyl" as used herein contemplates straight chain alkyl groups containing from one to three carbon atoms and includes methyl, ethyl and propyl.

The term "complex borohydride" as used herein contemplates the metal borohydrides, including sodium borohydride, potassium borohydride, lithium borohydride, zinc borohydride and the like, and metal trihydrocarbylborohydrides including lithium 9-alkyl-9-borabicyclo[3,3,1]nonylhydride, in which the alkyl contains one to seven carbon atoms, preferably lithium 9-tert-butyl-9-borabicyclo[3,3,1]-nonylhydride, prepared according to the procedure described in German Offenlegungsschrift 2,207,987, published Aug. 31, 1972, lithium diisopinocamphenyl-tert-butylborohydride and lithium 2-thexyl-4,8-dimethyl-2-borobicyclo[3,3,1]nonylhydride described by E. J. Corey et al., J. Amer. Chem. Soc., 93, 1491 (1971), lithium perhydro-9b-borophenalylhydride, described by H. C. Brown and W. C. Dickason, J. Amer. Chem. Soc., 92, 709 (1970) and the like.

The compounds of formula 1 possess interesting pharmacological properties when tested in standard pharmacological tests. In particular, they have been found to possess hypotensive, antihypertensive, bronchospasmolytic, gastric acid secretion inhibiting, abortifacient and estrus synchronizing and ovulation regulating properties, which make them useful in the treatment of conditions associated with high blood pressure, in the treatment of asthmatic conditions, in the treatment of pathological conditions associated with excessive secretion of gastric acid such as, for example, peptic ulcer, in population control, and in animal husbandry. In addition, the compound of this invention inhibit the aggregation of platelets and promote the disaggregation of aggregated platelets, and are useful as agents for the prevention and treatment of thrombosis.

More particularly, these compounds, when tested in a modification of the tests for determining hypotensive activities described in "Screening Methods in Pharmacology", Academic Press, New York and London 1965, page 146, using the cat in urethane-chloralose anaesthesia as the test animal and measuring mean arterial blood pressure before and after intravenous administration of the compounds, have exhibited utility as hypotensive agents. When tested in the renal hypertensive rat, prepared by the method of A. Grollman described in Proc. Soc. Exp. Biol. Med., 7, 102 (1954), and measuring blood pressure by the method described by H. Kersten, J. Lab. Clin. Med., 32, 1090 (1947), they have exhibited utility as antihypertensive agents.

Moreover, the compounds of this invention, when tested in a modification of the test method described by A. K. Armitage, et al., Brit. J. Pharmacol., 16, 59 (1961), have been found to alleviate bronchospasms, and are useful as bronchospasmolytic agents.

Furthermore, the compounds of this invention, when administered to rats in the test method described by H. Shay, et al., Gastroenterol., 26, 906 (1954), have been found to inhibit the secretion of gastric acid, and are useful as agents inhibiting the secretion of gastric acid.

In addition, the compounds of this invention, when tested in a modification of the test method described by G. V. R. Born, Nature, 194, 927 (1962), using the aggregometer manufactured by Bryston Manufacturing Limited, Rexdale, Ontario, Canada, have been shown to inhibit the aggregation of platelets and to promote the disaggregation of aggregated platelets, and are useful as agents for the prevention and treatment of thrombosis.

When the compounds of this invention are employed as hypotensive or anti-nypertensive agents, as agents inhibiting gastric acid secretion in warm-blooded animals, for example, in cats or rats, as agents for the prevention or treatment of thrombosis, or as bronchospasmolytic agents, alone or in combination with pharmacologically acceptable carriers, their proportions are determined by their solubilities, by the chosen route of administration, and by standard biological practice. The compounds of this invention may be administered orally in solid form containing such excipients as starch, lactose, sucrose, certain types of clay, and flavouring and coating agents. However, they are preferably administered parenterally in the form of sterile solutions thereof which may also contain other solutes, for example, sufficient sodium chloride or glucose to make the solution isotonic. For use as bronchospasmolytic agents, the compounds of this invention are preferably administered as aerosols.

The dosage of the present hypotensive, antihypertensive, gastric acid secretion inhibiting, or bronchospasmolytic agents, or agents for the prevention and treatment of thrombosis will vary with the forms of administration and the particular hosts under treatment. Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in range of from about 0.1 mg to about 10.0 mg per kilo, although as aforementioned variations will occur. However, a dosage level that is in the range of from about 0.5 mg to about 5 mg per kilo is most desirably employed in order to achieve effective results. When administering the compounds of this invention as aerosols the liquid to be nebulized, for example, water, ethyl alcohol, dichlorotetrafluoroethane and dichlorodifluoromethane, contain preferably from 0.005–0.05 per cent of the acid, or a non-toxic alkali metal, ammonium or amine salt thereof, or ester of formula 1.

Furthermore, when the compounds of this invention are tested by the method of A. P. Labhsetwar, Nature, 230, 528 (1971) whereby the compound is given subcutaneously on a daily basis to mated hamsters on days 4, 5 and 6 of pregnancy, thereafter the animals being sacrificed on day 7 of pregnancy and the number of abortions counted, the compounds are shown to have abortifacient properties.

For example, complete abortion resulted in all animals when the following compounds of formula 1 were tested according to this method at doses noted below:
trans, cis-7-[2-(3-hydroxy-3-methyl-1-octenyl)-5-oxocyclopentyl]-5-heptenoic acid (Example 59), 2.5 mg/kg/day,
trans, cis-7-[2-(3-hydroxy-3-methyl-1-octenyl)-5-oxocyclopentyl]-4-heptenoic acid (Example 59) 2.5 mg/kg/day, and
trans, cis-7-[2-hydroxy-5-(3-hydroxy-3-methyl-1-octenyl)cyclopentyl]-5-heptenoic acid (Example 75), 0.5 mg/kg/day.

The potency of the above unsaturated compounds is especially noteworthy in light of the fact that the completely saturated 15-methyl analog, 2-(3-hydroxy-3-methyloctyl)-5-oxocyclopentaneheptanoic acid, described in U.S. Pat. No. 3,671,570, cited above, does not cause complete abortion in the above test at doses less than 30 mg/kg/day.

Furthermore, the compounds of this invention are useful for inducing labor in pregnant animals at or near term. When the compounds of this invention are employed as agents for abortion or for inducing labor, the compounds are infused intravenously at a dose 0.01 to 100 mg/kg per minute until the desired effect is obtained.

Still furthermore, the compounds of formula 1 are useful for the synchronization of estrus and the regulation of ovulation in animals.

It is often desirable to synchronize estrus in domestic animals, for example, horses, cattle, sheep, swine or dogs, in order to be able to perform artificial insemination or mating with a male of the desired genetic quality under optimum conditions. In the past, this has been done by administering to the animals an ovulation-inhibiting agent, withdrawing administration of said agent shortly before the date chosen for mating or artificial insemination, and relying either upon the natural production of LH and FSH to induce ovulation and to produce estrus or by administering gonadotrophins. However, this procedure was not entirely satisfactory because ovulation at a predetermined time occured only in a certain proportion of the animals when gonadotrophins were not used. On the other hand, the high cost of gonadotrophins and side effects encountered in their administration made this method impractical. It is now possible to obtain substantially complete synchronization of ovulation and of estrus, by treating the animals in a given group with the compound of formula 1 before the predetermined period of time for mating or artificial insemination, so as to obtain ovulation and estrus within that time interval. The delay in the onset of ovulation and estrus following administration of the compound of this invention varies with the species of animal. For example, in rodents such as rats or hamsters ovulation takes place within 18 hours following administration of the compound and in the horse ovulation usually takes place within one week after the compound is given.

More specifically, synchronization of estrus and regulation of ovulation in the horse is achieved by giving the compound of formula 1, either randomly to a group of horses during the life of the corpus luteum (usually day 5 to day 16 of the cycle) or two to three days prior to the expected onset of estrus. The compound for example, trans, cis-7-[2α-hydroxy-5-(3-hydroxy-3-methyl-1-octenyl)cyclopentyl]-5-heptenoic acid, is given by intrauterine infusion, subcutaneously or intramuscularly in sterile solutions. A dosage which is in the range of from about 1 to 100 mg/1000 lb, preferably 5 to 25 mg/1000 lb is employed and is administered as a single dose or spread over a period of 72 hours. Practically speaking it is preferable to give one-half the total dose on two consecutive days for the latter form of administration. For example, in a group of horses receiving this medication on the second and third day before expected estrus, estrus follows within 24 to 48 hours which in turn is followed by ovulation occuring in the majority of animals, from the fourth to the sixth day thereafter as determined by rectal palpation of the ovaries.

In a control group receiving no medication the occurance of ovulation was spread rather unevenly over the third to eighth day after the onset of estrus.

The process of this invention may be illustrated as shown in the accompanying flow sheet.

With reference to the starting materials required for the above process, the aldehyde of formula L—CHO in which L is radical A wherein $R^5$ is ethyl has been described by D. T. Warner, J. Org. Chem., 24, 1536 (1959). By following the process described therein for the preparation of that aldehyde and using the appropriate di(lower)alkylbromomalonate the aldehydes of formula L—CHO in which L is radical A wherein $R^5$ is a lower alkyl other than ethyl are obtained.

The aldehyde of formula L—CHO in which L is the radical B or C is prepared according to the procedure described in the copending U.S. application Ser. No. 259,896, filed June 5, 1972. Briefly, these starting materials are prepared in the following manner (the symbols m and Z in the following description have the same significance as described hereinbefore): A lower alkyl ester of 2-(ω-carboxy—(CH$_2$)$_m$—Z—CH$_2$)cyclopent-2-en-1-one, preferably the methyl ester, conveniently prepared by treating a 2-(ω-carboxy—(CH$_2$)$_m$—Z—CH$_2$)cyclopent-2-en-1-one (7), see below, zane for the DMIS group or isobutylene for the tert-butyl group.

The lower alkyl ester of 2-(ω-carboxy—(CH$_2$)$_m$—Z—CH$_2$)cyclopent-2-en-1-one (7), noted above, is prepared by the following convenient process:

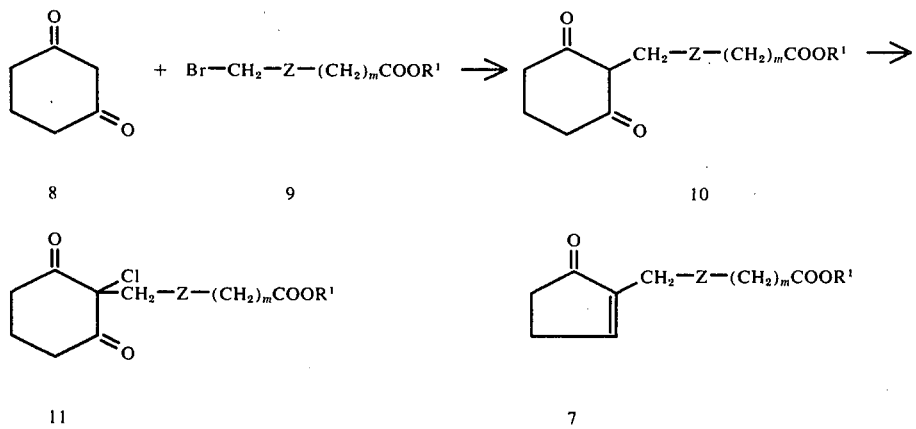

with a lower alkanol containing from 1–6 carbon atoms, preferably methanol, and p-toluenesulfonic acid, is treated with nitromethane in the presence of an alkali metal lower alkoxide, preferably sodium methoxide, to yield the corresponding lower alkyl ester, preferably the methyl ester, of a 2-(ω-carboxy—(CH$_2$)$_m$—Z—CH$_2$)-3-nitromethylcyclopentan-1-one. The 1-keto group of the latter is reduced with sodium borohydride to yield the corresponding lower alkyl ester of 2-(ω-carboxy—(CH$_2$)$_m$—Z—CH$_2$)-3-nitromethylcyclopentan-1-ol, preferably the methyl ester.

The latter two compounds, the 3-nitromethylcyclopentan-1-one and the 3-nitromethylcyclopentan-1-ol derivatives are converted to their respective aci-forms by treatment with a strong base such as an alkali metal lower alkoxide, preferably sodium methoxide, or an aqueous alkali metal hydroxide, preferably sodium hydroxide, and the resulting solution of the alkali metal salt of the corresponding nitronic acid is added to a cold aqueous solution of a mineral acid, preferably dilute sulfuric acid at a temperature in the range between about −10° C and about 25° C, preferably in the vicinity of 0° C. Extraction of the mixture with a water-immiscible solvent, preferably diethyl ether, and evaporation of the latter yields respectively the corresponding 3-aldehyde, namely the desired ketoaldehyde starting material of formula L—CHO in which L is the radical C and the unprotected hydroxyaldehyde, precursor to the desired starting material of formula L—CHO in which L is the radical B. The latter precursor is thereafter transformed into the desired starting material of formula L—CHO in which L is the radical B wherein R$^6$ is a radical suitable for protecting a hydroxy group, for example, tetrahydropyran-2-yl (THP), trimethylsilyl (TMS), dimethylisopropylsilyl (DMIS) and tert-butyl. Said transformation is effected by treating the precursor with a reagent known to be effective for converting a hydroxy group of a known compound to a protected hydroxy group. Such reagents include an excess of dihydropyran and an acid catalyst for example, p-toluenesulfonic acid, hydrogen chloride or sulfuric acid, for the THP group, trimethylchlorosilane with hexamethyldisilazane for the TMS group, dimethylisopropylchlorosilane and diisopropyltetramethyldisilain which Z and m are as defined in the first instance and R$^1$ is lower alkyl.

With reference to the first step of this process 1,3-cyclohexadione (8) is condensed with an appropriate lower alkyl ω-bromoester of formula 9 in the presence of an alkali metal alkoxide in a lower alkanol, preferably sodium methoxide in methanol, to give the dione of formula 10.

The latter compound is then treated with t-butyl hypochlorite in the manner described by G. Buchi and B. Egger, J. Org. Chem., 36, 2021 (1971), to yield the chloro derivative 11. The latter treatment is performed preferably under a nitrogen atmosphere using dry chloroform as a solvent. Thereafter, the chloro derivative is treated in a hydrocarbon solvent, preferably toluene, in the presence of an alkali metal carbonate, preferably sodium carbonate, at temperatures from 100° to 150° C from about 5 to 25 hours whereby ring contraction is effected to yield the desired lower alkyl ester of 2-(ω-carboxy—(CH$_2$)$_m$—Z—CH$_2$)cyclopent-2-en-1-one (7).

The ω-bromoacids and the lower alkyl ω-bromoesters of formula 9 utilized for the preparation of compound 7 are either known, for example, 7-bromo-5-heptenoic acid its corresponding ethyl ester and several homologs of these compounds are described in Belgian Pat. No. 766,520, published Nov. 3, 1971, or may be prepared by standard methods; for example, see "Rodd's Chemistry of the Carbon Compounds", S. Coffey, Ed., Vol. 1c, 2nd Ed., pp. 201–252 and the copending application, Ser. No. 238,650, filed Mar. 27, 1972.

In practising the process of this invention, the aldehyde of formula L—CHO in which L is the radical A, B or C is used as the starting material. This aldehyde is treated with a Wittig reagent of the formula (AlkO)$_2$POCH$_2$COCR$^3$R$^4$(CH$_2$)$_n$CH$_3$ in which Alk is an alkyl containing one to three carbon atoms and R$^3$, R$^4$ and n are as defined hereinbefore, in the presence of an alkali metal hydride, preferably sodium hydride, and in an aprotic solvent, preferably dimethoxyethane or dimethyl formamide. Acidification with an aqueous acid, preferably aqueous acetic acid, extraction with a water-immiscible solvent, preferably diethyl ether, followed by washing, drying and evaporation of the latter, yields the corresponding compound of formula L—CH=CH-CO—CR³R⁴—(CH₂)ₙCH₃.

The requisite Wittig reagents are prepared by the method of E. J. Corey and G. T. Kwiatkowski, J. Amer. Chem. Soc., 88, 5654 (1966) using the appropriate lower alkyl alkanoate and di(lower)alkyl α-lithiomethanephosphonate.

More specifically, the treatment of the aldehyde derivative of formula L—CHO in which L is the radical A, B or C with the ylid prepared from the Wittig reagent is performed in the following manner. A solution of the Wittig reagent in about 5 to 10 parts of an aprotic solvent, preferably dimethoxyethane or dimethylformamide, is added slowly under a blanket of nitrogen to a stirred suspension of approximately one equivalent of an alkali metal hydride, preferably sodium hydride, in approximately 150 parts of the aprotic solvent and stirring is continued at room temperature for a period of time of from 10 to 60 minutes, preferably for about 30 minutes. To the resulting solution of the corresponding ylid, there is slowly added a solution of approximately three quarters to one equivalent, preferably about 0.85 equivalent, of the aldehyde of formula L—CHO in about 5 to 10 parts, preferably about 8 parts of an aprotic solvent, preferably dimethoxyethane. The addition is carried out at 20° to 100° C, preferably 25° to 65° C over a period of time of from 5 to 60 minutes. Acidification with an aqueous acid, preferably aqueous acetic acid, followed by extraction with a water-immiscible solvent, preferably diethyl ether, washing and drying of the extracts, evaporation of the solvent, and chromatography of the residue on silica gel yields the corresponding compound of formula L—CH = CHCOCR³R⁴—(CH₂)ₙCH₃ (3) in which L is the radical A, B or C and R³, R⁴ and n are as defined hereinbefore.

Before proceeding further with the process of this invention it is expedient, in the case where L of the last-named compound of formula 3 represents the radical C, to protect the 1-keto group of the cyclopentanone ring of radical C. Said protection is advantageously afforded by treatment of the compound of formula 3 in which L is radical C with ethylene glycol in the presence of an acid catalyst, for example, p-toluenesulfonic acid, hydrogen chloride or sulfuric acid, in an inert solvent, for example, benzene or tetrahydrofuran. In this manner the corresponding compound of formula 3 is obtained in which L is the organic radical D, as defined hereinbefore, having said protected keto group.

Also it is worth noting at this point that a convenient alternative method has been found for the preparation of the compound of formula 3 in which L is the radical A as defined herein and R³, R⁴ and n are as defined in the first instance. In this latter method, the aldehyde of formula L—CHO in which L is the radical A is treated with a methyl ketone of formula CH₃COR⁹ in which R⁹ is CR³R⁴—(CH₂)ₙCH₃ in which R³, R⁴ and n are as defined in the first instance, in the presence of a base, to obtain the corresponding compound of formula 12,

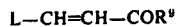    12, which in this case is the desired compound of formula 3 in which L is the radical A and R³, R⁴ and n are as defined in the first instance.

The aforementioned treatment of the aldehyde with the ketone of formula CH₃COR⁹ is performed preferably by using an organic base, for example, piperidine, N-methylpiperidine or N,N-dimethylpiperazine, although sodium hydride, potassium tert-butoxide, sodium ethoxide and the like are alternative suitable bases. If desired an inert solvent, for example, benzene, ether, dioxane or tert-butanol, is employed for this reaction. Although not critical, it is prudent to use substantially equivalent amounts of the aldehyde and the ketone for the reaction. Advantageous temperatures and times for this reaction include a temperature range of from 20° to 100° C, preferably 60° to 80° C, and a reaction time from 2 to 30 hours.

The instant compound of formula 3 in which L is the radical A, B or D is now converted to the corresponding compound of formula 4 by one of the following two methods depending on R² of the product being hydrogen or lower alkyl.

When it is desired to obtain the compound of formula 4 in which L is the radical A, B or D and R² is hydrogen, then the compound of formula 3 in which L is the radical A, B or D is treated with a metal borohydride, for example, lithium borohydride, potassium borohydride, zinc borohydride or preferably sodium borohydride, in an inert solvent, for example, methanol or tetrahydrofuran, to yield the desired compound of formula 4 as a mixture of epimers. The epimers result from the asymmetric center at the carbon to which the secondary alcohol is attached. The mixture of epimers need not be separated at this stage. In practice it has been found more convenient to continue the process with the mixture of epimers and, if desired, to separate the resulting epimers of compounds of formula 1.

When it is desired to obtain the compound of formula 4 in which L is the radical A or B and R² is lower alkyl then the latter compound of formula 3 in which L is the radical A or B is treated with a lower alkyl magnesium halide.

The addition of the lower alkyl magnesium halide to the last said compound of formula 3 is carried out according to the conditions of the Grignard reaction. Convenient and practical conditions for this addition include ether or tetrahydrofuran as the solvent for the reaction, a reaction time of from five minutes to six hours and a reaction temperature of from −80° to 25° C, preferably −70° to −40° C when L of the compound of formula 3 is radical A and preferably −20° to 0° C when L of the compound of formula 3 is radical B.

Alternatively, a convenient method for preparing the compound of formula 4 in which L is the radical A, R² is lower alkyl, R³ is hydrogen and R⁴ is hydrogen or lower alkyl and R⁷ is hydrogen, comprises treating the aldehyde of formula L—CHO in which L is the radical A with a methyl ketone of formula CH₃COR⁹ in which R⁹ is lower alkyl, in the presence of a base, to obtain the corresponding compound of formula 12,

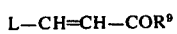    12 followed by treating the latter compound with an appropriate lower alkyl magnesium halide in which the alkyl portion is CR³R⁴—(CH₂)ₙCH₃ in which R³, R⁴ and n are as defined in the last instance. In this case the treatment of the aldehyde with the methyl ketone is performed according to the same conditions described hereinbefore for preparing the compound of formula 12 in which R⁹ is CR³R⁴—(CH₂)ₙCH₃. However, in this case it is advantageous to dispense altogether with an inert solvent for the reaction and to use a large excess of the ketone of formula $CH_3COR^9$, i.e. 10 to 100 equivalents, preferably 20 to 60 equivalents.

In other words, it is possible to use the compound of formula 12 in two ways to elaborate the side chain bearing the hydroxy group of the compound of formula 1. In the case where $R^9$ of formula 12 is $CR^3R^4—(CH_2)_nCH_3$, the $R^9$ group is the progenitor of part of the hydrocarbon reside of the side chain itself and in the case where $R^9$ is lower alkyl the $R^9$ group is the progenitor of the alkyl substituent on the side chain occurring when $R^2$ of the compound of formula 1 is lower alkyl.

From this point the process of this invention is completed by one of the following three methods depending on L of the compound of formula 4 being the radical A, B or D.

In the first method when L of the compound of formula 4 is the radical A, the cyclopropyl compound of formula 4 is condensed with a malonic ester derivative of formula 5,

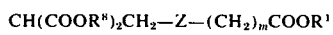

$$CH(COOR^8)_2CH_2—Z—(CH_2)_mCOOR^1 \qquad 5$$

in which $R^1$ and $R^8$ each are lower alkyl and Z and $m$ are as defined hereinbefore, in the presence of a base. If desired, but not critical, the hydroxy group of the compound of formula 4 may be protected during the course of this condensation. Suitably protection is afforded by reacting said last-named compound of formula 4 with the appropriate aforementioned reagent for providing a protected hydroxy group to afford the corresponding compound of formula 4 in which $R^7$ is a radical suitable for protecting a hydroxy group, for example, THP, TMS, DMIS or tert-butyl, see above.

The malonic ester derivative of formula 5, noted above, is prepared by condensing the appropriate aforementioned lower alkyl ω-bromoester of formula 9, with a dialkylmalonate, in the presence of an alkali metal alkoxide in a lower alkanol. More particularly, the condensation is performed preferably by adding the dialkylmalonate portionwise to a solution of one equivalent of sodium methoxide in methanol at a temperature of from 10° to 30° C, preferably room temperature. After stirring for about 10 to 20 minutes, the reaction mixture is treated portionwise with one equivalent of the bromoester of formula 9 followed by heating the reaction mixture at reflux temperature for 1 to 2 hours. Thereafter, dilution of the mixture with water, extraction with a water-immiscible solvent, preferably ether, washing and drying of the extract, followed by removal of the solvent gives a residue, which on purification by distillation under reduced pressure gives the desired malonic ester derivative of formula 5.

Alternatively the malonic ester derivative of formula 5 in which Z is $CH_2CH=CH—$ is prepared by treating a (2-formylethyl)malonic acid di(lower)alkyl ester, for example, (2-formylethyl)malonic acid diethyl ester, D. T. Warner and O. A. Moe, J. Amer. Chem. Soc., 70,3470 (1948), with a triphenylphosphonium bromide of formula

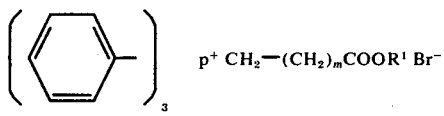

in which $R^1$ and $m$ are as defined hereinbefore in the presence of an alkali metal hydride, preferably sodium hydride, in an aprotic solvent, preferably dimethyl sulfoxide or dimethyl formamide, in the same manner as described previously for the treatment of the aldehyde of formula L—CHO with the Wittig reagent. In this manner the corresponding malonic ester derivative of formula $CH(COOR^8)_2CH_2CH_2CH=CH—(CH_2)_m COOR^1$ in which $R^1$, $R^8$ and $m$ are as defined hereinbefore is obtained. When $R^1$ of the latter compound is hydrogen, said latter compound is converted to the corresponding malonic ester derivative of formula 5 by treatment with a lower alkanol, for example, methanol or ethanol, in the presence of an acid catalyst, for example, p-toluenesulfonic acid, boron trifluoride etherate or dry hydrogen chloride.

The requisite triphenylphosphonium bromide of formula

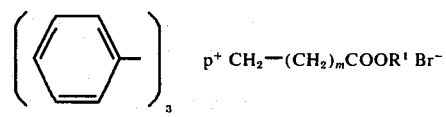

are prepared readily by treating the appropriate ω-bromoacid or ω-bromoester of formula Br $CH_2—(CH_2)_mCOOR^1$ in which $m$ is as defined hereinbefore with triphenylphosphine in an inert solvent, for example, benzene, or acetonitrile, at 20°–100° C for 12 to 24 hours and collecting the precipitate.

As noted previously the cyclopropyl compound of formula 4 and the malonic ester derivative of formula 5 are subjected to a base catalyzed condensation to give the cyclopentenonetriester of formula 6. This condensation is performed in the presence of a suitable base, preferably an alkali metal alkoxide, for example, sodium methoxide. Other suitable bases include sodium ethoxide, potassium tert-butoxide, and sodium hydride. More specifically, this condensation is conveniently effected by heating a mixture of about equimolar amounts of the compound of formula 4 and the triester 5 at 80 to 150° C, preferably 100°–140° C, for 30 minutes to 6 hours, preferably 1 to 3 hours. The reaction mixture is then cooled, neutralized with an acid, for example, acetic acid, and extracted with a water-immiscible solvent, for example, diethyl ether. Evaporation of the extract and purification of the residue by chromatography on silica gel yields the cyclopentanonetriester of formula 6.

Thereafter, in the case where the hydroxy group has been protected by a suitable protecting group, said group is now removed by an agent known to be effective for removing such a protecting group. In a preferred embodiment the base catalyzed condensation is effected with a compound of formula 4 in which $R^7$ is tetrahydropyran-2-yl and thereafter the tetrahydropyran-2-yl protecting group is removed by treating the resulting cyclopentanonetriester of formula 6 ($R^7$ = tetrahydropyran-2-yl) with acid, for example, hydrochloric acid, aqueous acetic acid or preferably p-toluenesulfonic acid, in an inert solvent in the presence of water, preferably methanol-water (9:1). Other agents for removing the protecting group are discussed hereinafter.

The cyclopentanonetriester 6 is now treated with an alkali metal hydroxide in the presence of water to give the corresponding compound of formula 1 in which $m$, $n$, Z, $R^2$, $R^3$ and $R^4$ are as defined in the first instance, X and Y together are oxo and $R^1$ is hydrogen. Preferably this reaction is done by heating a mixture of the cyclopentanonetriester with an alkali metal hydroxide, preferably sodium hydroxide or potassium hydroxide, in the presence of water at reflux temperature of the mixture for a period of 15 minutes to 6 hours, preferably about 1 to 3 hours. Neutralization of the reaction mixture with acid, for example, 2N HCl, extraction with a water-immiscible solvent, for example, diethyl ether, and subsequent work up of the extract yields an epimeric mixture of the said last-named compound of formula 1. If desired the epimers may be separated at this stage by chromatography on silica gel.

Thereafter, if desired the latter compound is esterified with a lower alkanol containing one to three carbon atoms, for example, methanol, ethanol or propanol, in the presence of a acid, for example, sulfuric acid, hydrochloric acid or preferably perchloric acid, to give the corresponding ester compound of formula 1 in which $m$, $n$, Z, $R^2$, $R^4$ are as defined in the first instance, X and Y together are oxo and $R^1$ is lower alkyl. Optionally, this esterification can be effected by treating said latter compound with an appropriate diazoalkane, for example, diazomethane, or diazoethane.

The second method, utilized when L of the aforementioned compound of formula 4 is the radical B, proceeds by treating the said compound of formula 4 with an agent known to be effective for removing a radical suitable for protecting a hydroxy group. In a preferred embodiment, L of the aforementioned compound of formula 4 is the radical B in which $R^6$ is the TMS radical. The TMS radical is removed by treatment with an excess of water-methanol (10:1) for 24 hours or with tetrahydrofuran-acetic acid at room temperature for 1 to 2 hours. Alternatively, if $R^6$ is DMIS, this protecting group is removed by the same conditions used for the removal of the TMS radical.

In this manner the compound of formula 1 in which $m$, $n$, Z, $R^2$, $R^3$ and $R^4$ are as defined in the first instance, X is hydroxy, Y is hydrogen and $R^1$ is lower alkyl is obtained. This compound is obtained thus as a mixture of epimers with respect to the hydroxy group of the cyclopentane ring. If desired the epimers can be separated readily by chromatography.

Furthermore, if so desired, the latter compounds of formula 1 in which $R^2$ is lower alkyl are treated with an oxidizing agent capable of converting a hydroxy function to the corresponding keto function to yield the corresponding compound of formula 1 in which X and Y together are oxo. Suitable oxidizing agents include chromium trioxide-pyridine complex, chromium trioxide-sulfuric acid in acetone, with the former being preferred.

The third method, utilized when L of the compound of formula 4 is the radical D and $R^2$ is hydrogen proceeds with preferential hydrolysis of the ketal. The hydrolysis is effected by treatment with an acid in the presence of water, in an inert solvent. Suitable conditions for this hydrolysis include the use of p-toluenesulfonic acid or acetic acid at a temperature of from 25° to 100° C using tetrahydrofuran, dioxane, acetone or methanol as the solvent and a reaction period of from 3 to 24 hours. Preferably, the hydrolysis is effected using p-toluenesulfonic acid in tetrahydrofuran or a mixture of water and methanol at room temperature for 12 to 24 hours.

In this manner the compound of formula 1 in which $m$, $n$, Z, $R^3$ and $R^4$ are as defined in the first instance, X and Y together are oxo, $R^1$ is lower alkyl and $R^2$ is hydrogen is obtained.

Finally, and if desired any of the aforementioned compounds of formula 1 in which X and Y together are oxo and $R^1$ is lower alkyl are reduced by treatment with a complex borohydride to give the corresponding compound of formula 1 in which X is hydroxy and Y is hydrogen.

This reduction is preferably carried out by treating the compound of formula 1 in which X and Y are oxo with sodium borohydride in an inert solvent, for example, ethanol or tetrahydrofuran at 0° to 30° C from 30 minutes to 2 hours or with lithium 9-tert-butyl-9-borobicyclo[3,3,1]nonylhydride in an inert solvent, for example, tetrahydrofuran, or diglymetetrahydrofuran at −80° to 0° C, preferably −80° to −60° C, for 1 to 2 hours. In this instance the resulting compound of formula 1 in which X is hydroxy and Y is hydrogen and $R^1$ is hydrogen or lower alkyl is obtained as a mixture of epimeric C-2 alcohols. This mixture is conveniently separated into its individual C-2 alcohol epimers by chromatography on silica gel.

The following examples illustrate further this invention.

EXAMPLE 1

Dimethyl 3,3-dimethyl-2-oxoheptyl phosphonate
[(AlkO)$_2$POCH$_2$COCR$^3$R$^4$—(CH$_2$)$_n$CH$_3$ in which Alk is CH$_3$, R$^3$ and R$^4$ = CH$_3$ and $n$ = 3]

The title compound is prepared by treating 2,2-dimethylhexanoic acid methyl ester, S. M. McElvain, et al., J. Amer. Chem Soc., 75, 3987 (1953), with dimethyl methyl phosphonate according to the procedure of E. J. Corey and G. T. Kwiatkowski, J. Amer. Chem. Soc., 88, 5654 (1966). An exemplification of this procedure is as follows:

Dimethyl methylphosphonate (14.88 g) is dissolved in dry tetrahydrofuran (THF, 34 ml) under a nitrogen atmosphere. The solution is cooled to −78° C. Butyllithium (7.68 g, 52 ml of 2.3 molar solution, 3 equiv.) is added very slowly during 1 hour. The mixture is stirred at −78° C for 15 minutes. A solution of 2,2-dimethylhexanoic acid methyl ester (6.32 g) in dry THF (16 ml) is added to the cold solution over a period of 1 hour. The mixture is stirred for 30 minutes and then allowed to warm up to room temperature. The reaction mixture is diluted with ether. Dilute (10%) hydrochloric acid (30 ml) is added and the reaction mixture shaken well. The organic phase is separated and washed several times with water, dried (MgSO$_4$) and the solvent removed. The residue is distilled under reduced pressure to give the title compound, b.p. 110°–120° C/O.1mm, $\gamma_{max}^{film}$ 1700, 1250, 1020 cm$^{-1}$.

Similarly other Wittig reagents of the formula (AlkO)$_2$POCH$_2$COCR$^3$R$^4$—(CH$_2$)$_n$CH$_3$ in which Alk is an alkyl containing one to three carbon atoms, R$^3$ and R$^4$ are hydrogen or lower alkyl and $n$ is an integer from two to five are prepared by using the appropriate lower alkyl alkanoate and di(lower)alkyl methanephosphonate. For instance, treatment of 2,2-dipropylpentanoic acid methyl ester with dimethyl methylphosphonate gives 2-oxo-3,3-dipropylhexyl phosphonate and treatment of 2,2-diethyloctanoic acid ethyl ester with diethyl methylphosphonate gives 2-oxo-3,3-diethylnonyl phosphonate.

EXAMPLE 2

Dimethyl 2-formylcyclopropane-1,1-dicarboxylate (2; L = radical A in which $R_5 = CH_3$)

By following the procedure of D. T. Warner, cited above, used for preparing diethyl 2-formylcyclopropane-1,1-dicarboxylate from acrolein but using equivalent amounts of dimethylbromomalonate and methanol instead of diethylbromomalonate and ethanol, respectively, the title compound, nmr (CDCl$_3$) δ 1.98 (m, 2H), 2.80 (m, 1H), 3.79 (s, 6H), 8.82 (d, J = 4 cps, 1H), is obtained.

Likewise the use of dipropylbromomalonate and propanol gives dipropyl 2-formylcyclopropane-1,1-dicarboxylate.

EXAMPLE 3

Diethyl trans-2-(4,4-dimethyl-3-oxo-1-octenyl)cyclopropane-1,1-dicarboxylate (3; $R^3$ and $R^4 = CH_3$, $n = 3$ and L = radical A in which $R^5 = C_2H_5$)

To a suspension of 50% sodium hydride (0.46 g, washed with hexane) in dimethylformamide (DMF) is added a solution of dimethyl 3,3-dimethyl-2-oxoheptyl phosphonate (2.75 g), described in Example 1, in DMF (15 ml) over a period of 30 min. The mixture is stirred and cooled in ice water during the addition and for an additional period of 45 min. A solution of diethyl 2-formylcyclopropane-1,1-dicarboxylate (2.14 g) in DMF (15 ml) is added over 20 min. The reaction mixture is heated at 55° to 60° C and stirred for 45 min. The mixture is now cooled in an ice bath and acetic acid is added to render the mixture substantially neutral. The reaction mixture is poured into water (4 × the volume) and the resulting oily precipitate extracted with ether. The extract is washed with water, dried (Na$_2$SO$_4$) and concentrated. The residue is dissolved in ethyl acetate-benzene (1:9) and the solution poured through a column of silica gel (148 g). The eluate is concentrated to yield the title compound, $\gamma_{max}^{film}$ 1725, 1680, 1620 cm$^{-1}$, nmr (CDCl$_3$) δ 0.88 (t, 3H), 4.27 (4H), 6.5, 6.68 and 7.39 (m, 2H), $\lambda_{max}^{EtOH}$ 242 nm (ε 32 7500).

In the same manner but replacing diethyl 2-formylcyclopropane-1,1-dicarboxylate with dimethyl 2-formylcyclopropane-1,1-dicarboxylate, dimethyl trans-(4,4-dimethyl-3-oxo-1-octenyl)cyclopropane-1,1-dicarboxylate, $\gamma_{max}^{film}$ 1728, 1682 cm$^{-1}$, is obtained.

In the same manner but replacing dimethyl 3,3-dimethyl-2-oxoheptyl phosphonate with an equivalent amount of dimethyl 3-methyl-2-oxoheptyl phosphonate, b.p. 112°–115° C/0.2 mm, prepared from 2-methylhexanoic acid methyl ester or the 2-methylhexanoic acid chloride according to the procedure of Example 1, diethyl trans-2-(4-methyl-3-oxo-1-octenyl)cyclopropane-1,1-dicarboxylate, $\gamma_{max}^{film}$ 1725, 1680, 1665, 1620 cm$^{-1}$, nmr (CDCl$_3$) δ 4.19 (q, J = 7, 4H), 6.32 (d, J = 5, 2H), is obtained.

In the same manner but replacing dimethyl 3,3-dimethyl-2-oxoheptyl phosphonate with an equivalent amount of dimethyl 2-oxoheptyl phosphonate, described by E. J. Corey, et al., J. Amer. Chem. Soc., 90, 3247 (1968), diethyl trans-2-(3-oxo-1-octenyl)cyclopropane-1,1-dicarboxylate, b.p. 153°–154° C/0.7 mm, is obtained.

In the same manner but replacing dimethyl 3,3-dimethyl-2-oxoheptylphosphonate with an equivalent amount of dimethyl 3-ethyl-2-oxohexyl phosphonate, dimethyl 3-propyl-2-oxooctyl phosphonate, or dimethyl 3-ethyl-2-oxononyl phosphonate, dimethyl trans-2-(4-ethyl-3-oxo-1-heptenyl)cyclopropane-1,1-dicarboxylate, dimethyl trans-2-(3-oxo-4-propyl-1-nonenyl)cyclopropane-1,1-dicarboxylate and dimethyl trans-2-(4-ethyl-3-oxo-1-decenyl)cyclopropane-1,1-dicarboxylate are obtained, respectively.

By following the procedure of Example 3 and utilizing the appropriate Wittig reagent and the aldehyde of formula L—CHO in which L is the radical A wherein $R^5$ is lower alkyl then other compounds of formula 3 are obtained. Examples of such compounds of formula 3 are listed in Table I together with the appropriate Wittig reagent and aldehyde of formula L—CHO utilized for their preparation.

TABLE I

| Ex. | Wittig Reagent (AlkO$_2$)POCH$_2$COCR$^3$R$^4$-(CH$_2$)$_n$CH$_3$ | | | | L-CHO L = radical A | Product: (Prefix Listed below)-cyclopropane 1,1-dicarboxylate |
|---|---|---|---|---|---|---|
| | Alk | R$^3$ | R$^4$ | N | R$^5$ | |
| 4 | CH$_3$ | H | H | 2 | CH$_3$ | dimethyl trans-2-(3-oxo-1-heptenyl) |
| 5 | CH$_3$ | H | H | 4 | C$_2$H$_5$ | diethyl trans-2-(3-oxo-1-nonenyl) |
| 6 | CH$_3$ | H | H | 5 | CH$_3$ | dimethyl trans-2-(3-oxo-1-decenyl) |
| 7 | CH$_3$ | CH$_3$ | H | 2 | C$_2$H$_5$ | diethyl trans-2-(4-methyl-3-oxo-1-heptenyl) |
| 8 | CH$_3$ | CH$_3$ | H | 4 | CH$_3$ | dimethyl trans-2-(4-methyl-3-oxo-1-nonenyl) |
| 9 | CH$_3$ | C$_2$H$_5$ | H | 3 | C$_2$H$_5$ | diethyl trans-2-(4-ethyl-3-oxo-1-octenyl) |
| 10 | CH$_3$ | C$_2$H$_5$ | H | 5 | CH$_3$ | dimethyl trans-2-(4-ethyl-3-oxo-1-decenyl) |
| 11 | CH$_3$ | n-C$_3$H$_7$ | H | 2 | C$_2$H$_5$ | diethyl trans-2-(3-oxo-4-propyl-1-heptenyl) |
| 12 | CH$_3$ | n-C$_3$H$_7$ | H | 4 | CH$_3$ | dimethyl trans-2-(3-oxo-4-propyl-1-nonenyl) |
| 13 | C$_2$H$_5$ | CH$_3$ | CH$_3$ | 5 | n-C$_3$H$_7$ | dipropyl trans-2-(4,4-dimethyl-3-oxo-1-decenyl) |
| 14 | C$_2$H$_5$ | C$_2$H$_5$ | CH$_3$ | 5 | n-C$_3$H$_7$ | dipropyl trans-2-(4-ethyl-4-methyl-3-oxo-1-decenyl) |
| 15 | C$_2$H$_5$ | n-C$_3$H$_7$ | CH$_3$ | 2 | CH$_3$ | dimethyl trans-2-(4-methyl-3-oxo-4-propyl-1-heptenyl) |
| 16 | C$_2$H$_5$ | n-C$_3$H$_7$ | n-C$_3$H$_7$ | 4 | C$_2$H$_5$ | diethyl trans-2-(3-oxo-4,4-dipropyl-1-nonenyl) |

EXAMPLE 17

Diethyl trans-2-(3-hydroxy-4,4-dimethyl-1-octenyl)cyclopropane-1,1-dicarboxylate (4; $R^2$ and $R^7$ = H, $R^3$ and $R^4$ = $CH_3$, $n$ = 3 and L = radical A in which $R^5$ = $C_2H_5$)

Sodium borohydride (0.19 g) is added to a solution of diethyl trans-2-(4,4-dimethyl-3-oxo-1-octenyl)cyclopropane-1,1-dicarboxylate (1.62 g), described in Example 3, in ethanol (2.5 ml) at 0° to 5° C. After the addition the mixture is rendered neutral by the addition of acetic acid, diluted with ether and washed with water. The ether phase is dried ($Na_2SO_4$) and concentrated. The residue is dissolved in ethyl acetate-benzene (1:9) and the solution poured through a column of silica gel (50 g). The eluate is concentrated to give the title compound, $\gamma_{max}^{film}$ 3500, 1706 $cm^{-1}$, nmr ($CDCl_3$) $\delta$ 2.6 (m, 1H), 3.78 (m, 1H), 4.21 (q, 4H), 5.28 (q, 1H), 5.9 (q,1H).

In the same manner but replacing diethyl trans-2-(4,4-dimethyl-3-oxo-1-octenyl)cyclopropane-1,1-dicarboxylate with an equivalent amount of diethyl trans-2-(4-methyl-3-oxo-1-octenyl) cyclopropane-1,1-dicarboxylate, described in Example 3, diethyl trans-2-(3-hydroxy-4-methyl-1-octenyl)cyclopropane-1,1-dicarboxylate, $\gamma_{max}^{film}$ 3500 $cm^{-1}$, is obtained.

By following the procedure of Example 17 and utilizing the appropriate compound of formula 3 then other compounds of formula 4 ($R^2$ = H) are prepared. Examples of such compounds of formula 4 are listed in Table II. In each case the compound of formula 3 used as starting material is noted by the Example in which it is prepared.

magnesium turnings and 157 g of methyl iodide in 1000 ml of ether, is cooled to −70° C. Diethyl trans-2-(3-oxo-1-octenyl)cyclopropane-1,1-dicarboxylate (124.2 g); described in Example 3, in 600 ml ether is added slowly taking care that reaction mixture temperature does not exceed −45° C. The mixture is stirred 75 min. at the temperature range −50° to −45° C. Aqueous saturated $NH_4Cl$ solution is added slowly keeping the temperature of the reaction mixture below −55° C. The mixture is diluted with water and extracted with 1500 ml ether. The ether layer is washed with saturated NaCl solution twice, then with 10% sodium thiosulfate solution twice, again with saturated NaCl solution, dried ($Na_2SO_4$) and concentrated to give a greenish yellow oil. The oil is dissolved in ethyl acetate-benzene (3:17) and poured through a column of silica gel. The eluate is concentrated to yield the title compound, nmr ($CDCl_3$) $\delta$ 0.88 (t, J = 5, 3H), 2.45 (q, 2H), 4.13 (q, 2H), 5.14 (2×d, J = 16.8, 1H), 5.72 (d, J = 16, 1H).

In the same manner but replacing methyl magnesium iodide with an equivalent amount of ethyl magnesium chloride, or propyl magnesium bromide, diethyl trans-2-(3-ethyl-3-hydroxy-1-octenyl)cyclopropane-1,1-dicarboxylate and diethyl trans-2-(3-hydroxy-3-propyl-1-octenyl)cyclopropane-1,1-dicarboxylate, are obtained, respectively.

In the same manner but replacing diethyl trans-2-(3-oxo-1-octenyl)cyclopropane-1,1-dicarboxylate with an equivalent amount of diethyl trans-2-(4-methyl-3-oxo-1-octenyl)cyclopropane-1,1-dicarboxylate, described in Example 3 and using methyl magnesium iodide, ethyl magnesium chloride or propyl magnesium bromide as the lower alkyl magnesium halide, diethyl trans-2-(3-

TABLE II

| EXAMPLE | NO. OF EXAMPLE IN WHICH STARTING MATERIAL OF FORMULA 3 IS PROPANE-1,1-DICARBOXYLATE | PRODUCT: (PREFIX LISTED BELOW)-CYCLO- |
|---|---|---|
| 18 | 3 | dimethyl trans-2-(4-ethyl-3-hydroxy-1-heptenyl) |
| 19 | 3 | diethyl trans-2-(3-hydroxy-4-propyl-1-nonenyl) |
| 20 | 3 | dimethyl trans-2-(4-ethyl-3-hydroxy-1-decenyl) |
| 21 | 7 | diethyl trans-2-(3-hydroxy-4-methyl-1-heptenyl) |
| 22 | 8 | dimethyl trans-2-(3-hydroxy-4-methyl-1-nonenyl) |
| 23 | 9 | diethyl trans-2-(4-ethyl-3-hydroxy-1-octenyl) |
| 24 | 10 | dimethyl trans-2-(4-ethyl-3-hydroxy-1-decenyl) |
| 25 | 11 | diethyl trans-2-(3-hydroxy-4-propyl-1-heptenyl) |
| 26 | 12 | dimethyl trans-2-(3-hydroxy-4-propyl-1-nonenyl) |
| 27 | 13 | dipropyl trans-2-(3-hydroxy-4,4-dimethyl-1-decenyl) |
| 28 | 14 | dipropyl trans-2-(4-ethyl-3-hydroxy-4-methyl-1-decenyl) |
| 29 | 15 | dimethyl trans-2-(3-hydroxy-4-methyl-4-propyl-1-heptenyl) |
| 30 | 16 | diethyl trans-2-(3-hydroxy-4,4-dipropyl-1-nonenyl) |

EXAMPLE 31

Diethyl trans-2-(3-hydroxy-3-methyl-1-octenyl)cyclopropane-1,1-dicarboxylate (4; $R^2$ = $CH_3$, $R^3$, $R^4$ and $R^7$ = H, $n$ = 3 and L = radical A in which $R^5$ = $C_2H_5$)

A solution of the lower alkyl magnesium halide, methyl magnesium iodide, prepared from 24.31 g of hydroxy-3,4-dimethyl-1-octenyl)cyclopropane-1,1-dicarboxylate, diethyl trans-2-(3-ethyl-3-hydroxy-4-methyl-1-octenyl)cyclopropane-1,1-dicarboxylate and diethyl trans-2-(3-hydroxy-4-methyl-3-propyl-1-octenyl)cyclopropane-1,1-dicarboxylate, are obtained, respectively.

By following the procedure of Example 31 and utilizing the appropriate lower alkyl magnesium halide and compound of formula 3, for example those described in Examples 4 to 12, then other compounds of formula 4 in which $R^2$ is lower alkyl are obtained. Examples of such compounds of formula 4 are listed in Table III together with the requisite lower alkyl magnesium halide and the compound of formula 3.

TABLE III

| EXAMPLE | NO. OF EXAMPLE IN WHICH STARTING MATERIAL OF FORMULA 3 IS PREPARED | LOWER ALKYL MAGNESIUM HALIDE | PRODUCT: (PREFIX: LISTED BELOW)-CYCLOPROPANE-1,1-DICARBOXYLATE |
|---|---|---|---|
| 32 | 4 | $CH_3MgI$ | dimethyl trans-2-(3-hydroxy-3-methyl-1-heptenyl) |
| 33 | 5 | $C_2H_5MgBr$ | diethyl trans-2-(3-ethyl-3-hydroxy-1-nonenyl) |
| 34 | 6 | $n$-$C_3H_7MgCl$ | dimethyl trans-2-(3-hydroxy-3-propyl-1-decenyl) |
| 35 | 7 | $CH_3MgBr$ | diethyl trans-2-(3-hydroxy-3,4-dimethyl-1-heptenyl) |
| 36 | 8 | $C_2H_5MgCl$ | dimethyl trans-2-(3-ethyl-3-hydroxy-4-methyl-1-nonenyl) |
| 37 | 9 | $n$-$C_3H_7MgCl$ | diethyl trans-2-(4-ethyl-3-hydroxy-3-propyl-1-octenyl) |
| 38 | 10 | $CH_3MgI$ | dimethyl trans-2-(4-ethyl-3-hydroxy-3-methyl-1-decenyl) |
| 39 | 11 | $C_2H_5MgCl$ | diethyl trans-2-(3-ethyl-3-hydroxy-4-propyl-1-heptenyl) |
| 40 | 12 | $n$-$C_3H_7MgCl$ | dimethyl trans-2-(3-hydroxy-3,4-dipropyl-1-nonenyl) |

EXAMPLE 41

Diethyl trans-2-{3-[(tetrahydropyran-2-yl)oxy]-3-methyl-1-octenyl}cyclopropane-1,1-dicarboxylate (4, $R^2 = CH_3$, $R^3$ and $R^4 = H$, $R^7 = $ (tetrahydropyran-2-yl)oxy, $n = 3$ and L = radical A in which $R^5 = C_2H_5$)

A solution of diethyl trans-2-(3-hydroxy-3-methyl-1-octenyl)cyclopropane-1,1-dicarboxylate (22.4 g), described in Example 31, dihydropyran (80 ml, distilled over sodium) and p-toluenesulfonic acid monohydrate (300 mg) is allowed to stand at room temperature for 30 min. After adding a few ml of 10% $Na_2CO_3$ solution the mixture is extracted with ether. The ether extract is washed with water, dried ($Na_2SO_4$) and evaporated. Purification of the residue by chromatography on silica gel gives the title compound, nmr ($CDCl_3$) δ 0.87 (t, 3H), 2,48 (m, 1H), 4.6 (1H), 5.5 (m, 2H).

In the same manner but using an equivalent amount of one of the compounds of formula 4 ($R^7 = H$), for example, the compounds listed in Examples 17 to 40, instead of diethyl trans-2-(3-hydroxy-3-methyl-1-octenyl)cyclopropane-1,1-dicarboxylate, then the corresponding tetrahydropyranyl ether compound of formula 4 ($R^7 = $ tetrahydropyranyl) is obtained, for example, the corresponding tetrahydropyranyl ether compounds of Examples 17 to 40, respectively. More specifically exemplified, in the same manner diethyl trans-2-(3-hydroxy-4-methyl-1-octenyl)cyclopropane-1,1-dicarboxylate, described in Example 17 gives diethyl trans-2-{3-[(tetrahydropyran-2-yl)oxy]-4-methyl-1-octenyl}-cyclopropane-1,1-dicarboxylate, $\gamma_{max}^{film}$ 1035, 1140, 1220 cm$^{-1}$, and dimethyl trans-2-(4-ethyl-3-hydroxyl-1-decenyl)cyclopropane-1,1-dicarboxylate, described in Example 24, gives dimethyl trans-2-{4-ethyl-3-[(tetrahydropyran-2-yl)oxy]-1-decenyl}-cyclopropane-1,1-dicarboxylate.

EXAMPLE 42

Trimethyl cis-3-heptene-1,1,7-tricarboxylate (5, $R^1$ and $R^8 = CH_3$, $Z = -CH = CHCH_2-$ and $m = 2$)

Dimethyl malonate (39.6 g) is added slowly with cooling and stirring to a solution of 6.9 g of sodium dissolved in 100 ml of absolute methanol and the mixture stirred for 15 min. The bromoester of formula 9, methyl cis-7-bromo-5-heptenoate (65.7 g) is added dropwise. The mixture is heated at reflux for 1 hr., cooled and diluted with water. The mixture is extracted with ether. The ether extracts are dried ($Na_2SO_4$) and concentrated. The residue is distilled under reduced pressure to give the title compound, b.p. 140°–150° C/0.7 mm.

The title compound is also described in copending application Ser. No. 238,650, filed Mar. 27, 1972.

In the same manner but replacing methyl cis-7-bromo-5-heptenoate with an equivalent amount of methyl 7-bromo-4-heptenoate, methyl 6-bromo-4-hexenoate, methyl 6-bromo-3-hexenoate, methyl 5-bromo-3-pentenoate, methyl 5-bromo-2-pentenoate, methyl 7-bromoheptanoate, methyl 6-bromohexanoate or methyl 5-bromohexanoate, trimethyl 4-heptene-1,1,7-tricarboxylate, trimethyl 3-hexene-1,1,6-tricarboxylate, trimethyl 4-hexene-1,1,6-tricarboxylate, trimethyl 3-pentene-1,1,5-tricarboxylate, trimethyl 4-pentene-1,1,5-tricarboxylate, trimethyl heptane-1,1,7-carboxylate, trimethyl hexane-1,1,6-tricarboxylate and trimethyl pentane-1,1,5-tricarboxylate are obtained, respectively.

By using the corresponding ethyl or other lower alkyl ester analogs of the methyl ester starting materials noted above, the corresponding ethyl or other lower alkyl esters of the methyl ester products, noted above, are obtained.

The following example discloses an alternative preparation of the above $\Delta^4$ triesters of formula V.

EXAMPLE 43

Triethyl cis-4-heptene-1,1,7-tricarboxylate (5, $R^1$ and $R^8 = C_2H_5$, $Z = -CH_2CH=CH-$ and $m = 2$)

For the following reaction, butyric acid triphenylphosphonium bromide, m.p. 245°–246° C, is prepared by treating γ-bromobutyric acid (100 g) with triphenyl phosphine in benzene (630 ml) at reflux temperature for 16 hr. and recrystallizing the resulting precipitate from ethanol.

Sodium hydride (50%, 19.46 g) is dissolved in dimethylsulfoxide (404 ml) with warming (70°–80° C) under a nitrogen atmosphere. The solution is cooled to 15° to 20° C. A solution of butyric acid triphenylphosphonium bromide (86.99 g) in dimethylsulfoxide is added. The mixture is stirred at the latter temperature for 5 min. and then treated dropwise with (2-formylethyl)malonic acid diethyl ester (39.7 g), described by Warner and Moe, cited above, over a period of 20 min. The mixture is stirred at room temperature for 2½ hr. and then cooled (10°–20° C) and rendered acidic with acetic acid (60 ml). The reaction mixture (pH = about 6) is poured into 2½ liters of ice water. After extraction with ether (2×), the aqueous layer is rendered acidic with concentrated hydrochloric acid to pH = 3 and extracted with ether (2×). The ether extracts are combined and washed with water (2×), then extracted with 10% $Na_2CO_3$ solution (3 × 200 ml). The aqueous sodium carbonate extracts are washed with ether (2×) and rendered acidic with conc HCl to pH 5. The acidic solution is extracted with ether (2×). The ether extracts are washed with water, dried and concentrated to dryness to give 1,1-diethyl cis-4-heptene-1,1,7-tricarboxylate.

The latter compound (21.4 g) in absolute ethanol (214 ml) is heated at reflux with p-toluenesulfonic acid (0.214 g) for 20 hr. After cooling to room temperature the reaction mixture is treated with 4 ml of pyridine and then diluted with water (750 ml). The mixture is extracted with ether. The ether extract is washed with water, dried ($MgSO_4$) and concentrated to give the title compound, $\gamma_{max}^{film}$ 1735 $cm^{-1}$.

In the same manner other $\Delta^4$-triesters of formula 5, namely triethyl 4-hexene-1,1,6-tricarboxylate and triethyl 4-pentene-1,1,5-tricarboxylate, are prepared by replacing butyric acid triphenylphosphonium bromide with propionic acid triphenyl phosphonium bromide and acetic acid triphenyl phosphonium bromide, respectively.

EXAMPLE 44

Dimethyl cis, trans-3-(6-carbomethoxy-2-hexenyl)-4-(3-hydroxy-4,4-dimethyl-1-octenyl)-2-oxo-1,3-cyclopentanedicarboxylate (6, $m = 2$, $n = 3$, $Z = -CH=CHCH_2-$, $R^1$, $R^3$, $R^4$, $R^5$ and $R^8 = CH_3$ and $R^2$ and $R^7 = H$)

To a solution of trimethyl cis-3-heptene-1,1,7-tricarboxylate (1.36 g), described in Example 42, in 3 ml of methanol, a freshly prepared solution of sodium methoxide (from 0.126 g of sodium and 6 ml of absolute methanol) is added. The mixture is heated to 80° C. A solution of dimethyl trans-(4,4-dimethyl-3-hydroxy-1-octenyl)cyclopropane-1,1-dicarboxylate (1.7 g) is gradually added to the mixture and the resulting mixture stirred for an additional 15 min. The methanol is removed by distillation at reduced pressure. The residue is then heated at 100° C for 45 min. Thereafter the mixture is cooled in an ice bath and rendered neutral with acetic acid. The mixture is extracted with ether. The extract is dried ($Na_2SO_4$) and concentrated. Chromatography of the residue on silica gel using ethyl acetate-benzene (1:4) as eluant gives the title compound, nmr ($CDCl_3$) δ 0.88 (3×m, 9H), 3.68–3.8 (3×m, 9H), 5.5 (2×m, 4H).

EXAMPLE 45

Diethyl cis, trans-3-(6-carboethoxy-2-hexenyl)-4-(3-hydroxy-3-methyl-1-octenyl)-2-oxo-1,3-cyclopentanedicarboxylate (6, $m = 2$, $n = 3$, $Z = -CH=CHCH_2-$, $R^1$, $R^5$ and $R^8 = C_2H_5$, $R^2 = CH_3$, $R^3$, $R^4$ and $R^7 = H$)

To a mixture of the compound of formula 4, diethyl trans-2-{3-[(tetrahydropyran-2-yl)oxy]-3-methyl-1-octenyl}cyclopropane-1,1-dicarboxylate (20.4 g), described in Example 41, and the compound of formula 5, triethyl cis-3-heptene-1,1,7-tricarboxylate (15.08 g), described in Example 42, a solution of 1.27 g of sodium in 50 ml of methanol is added at room temperature. The methanol is removed under slightly reduced pressure. The residue is heated at 135°–140° C for 1 hr. while keeping a slightly reduced pressure in the reaction flask. Saturated NaCl solution is added and the mixture rendered neutral with acetic acid. The mixture is extracted with ether. The extract is dried ($Na_2SO_4$) and concentrated. Chromatography of the residue on silica gel [eluant = ethyl acetate-benzene (1:4) yields diethyl cis, trans-3-(6-carboethoxy-2-hexenyl)-4-{3-[(tetrahydropyran-2-yl)oxy]-3-methyl-1-octenyl}-2-oxo-1,3-cyclopentanedicarboxylate, $\gamma_{max}^{EtOH}$ 291 nm ϵ = 13,400) in the presence of base (NaOH).

A solution of the latter compound (10.5 g) in 80 ml of methanol-water (9:1) and 1.0 g of p-toluenesulfonic acid monohydrate is left at room temperature for 15 min. and then rendered neutral with aqueous $NaHCO_3$. The methanol is evaporated and after addition of saturated NaCl, the mixture is extracted with ether. The ether layer is dried ($Na_2SO_4$). Evaporation of the solvent gives a residue, which on purification by chromatography on silica gel affords the title compound, nmr ($CDCl_3$) δ 0.84 (t, J = 6, 3H), 1.22 (2×m, 6H), 4.16 (m 6H), 5.35 (m, 2H), 5.56 (m, 2H).

By following the procedures of Examples 44 and 45 and using the appropriate compounds of formulae 4 and 5 as starting materials, other cyclopentanonetriesters of formula 6 are obtained.

For example, the use of the compound of formula 4, diethyl trans-2-{3-[(tetrahydropyran-2-yl)oxy]-3-methyl-1-octenyl}cyclopropane-1,1-dicarboxylate, described in Example 41, and the compound of formula 5, triethyl heptane-1,1,7-tricarboxylate, described in Example 42, in the procedure of Example 45 gives diethyl trans-3-(6-carboethoxyhexanyl)-4-(3-hydroxy-3-methyl-1-octenyl)-2-oxo-1,3-cyclopentanedicarboxylate, $\gamma_{max}^{film}$ 3500, 1725 $cm^{-1}$, nmr ($CDCl_3$) δ 0.88 (t, 3H), 4.17 (m, 6H), 5.64 (m, 2H), via the intermediate diethyl trans-3-(6-carboethoxyhexanyl)-4-{3-[(tetrahydropyran-2-yl)oxy]-3-methyl-1-octenyl}-2-oxo-1,3-cyclopentanedicarboxylate, $\gamma_{max}^{film}$ 1730 $cm^{-1}$.

Likewise, the use of diethyl trans-2-{3-[(tetrahydropyran-2-yl)oxy]-4-methyl-1-octenyl}cyclopropane-1,1-dicarboxylate and triethyl cis-3-heptene-1,1,7-tricarboxylate gives diethyl cis, trans-3-(6-carboethoxy-2-hexenyl)-4-(3-hydroxy-4-methyl-1-octenyl)-2- oxo-1,3-cyclopentanedicarboxylate, $\gamma_{max}^{film}$ 3500 cm$^{-1}$, $\lambda_{max}^{EtOH}$ 291 nm ($\epsilon$ = 13,600) in the presence of base (NaOH).

Likewise, the utilization of diethyl trans-2- 3-[(tetrahydropyran-2-yl)oxy]-3-methyl-1-octenyl cyclopropane-1,1-dicarboxylate, and triethyl cis-4-heptene-1,1,7-tricarboxylate, described in Example 43, gives diethyl cis, trans-3-(6-carboethoxy-3-hexenyl)-4-(3-hydroxy-3-methyl-1-octenyl)-2-oxo-1,3-cyclopentanedicarboxylate, nmr (CDCl$_3$) δ 0.89 (t, J = 5, 3H), 1.13 to 1.4 (m, 6H), 2.33 (2H), 4.2 (m, 2H), 5.4 (m, 2H), 5.65 (m, 2H).

Additional examples of compounds of formula 6 are listed in Table III together with the requisite starting materials. It is to be noted that when the procedure of Example 45 is used the requisite starting material of formula 4 is the corresponding tetrahydropyran-2-yl ether derivative of the compound of formula 4 noted therein; the tetrahydropyran-2-yl ether being prepared by following the procedure described in Example 41. Preparation of the starting materials of formula 5, i.e. triesters of formula 5, is described in Examples 42 and 43.

TABLE III

| EX. | NO. OF EXAMPLE IN WHICH STARTING MATERIAL OF FORMULA 4 IS DESCRIBED | STARTING MATERIAL OF FORMULA 5 | | | PRODUCT: (PREFIX LISTED BELOW)-2-OXO-1,3-CYCLO-PENTANEDICARBOXYLATE |
|---|---|---|---|---|---|
| | | Z | m | R$^1$ and R$^3$ | |
| 46 | 18 | (CH$_2$)$_3$ | 2 | CH$_3$ | dimethyl trans-3-(6-carbomethoxyhexyl)-4-(4-ethyl-3-hydroxy-1-heptenyl) |
| 47 | 19 | CH=CHCH$_2$ | 1 | C$_2$H$_5$ | diethyl cis,trans-3-(5-carboethoxy-2-pentenyl)-4-(3-hydroxy-4-propyl-1-nonenyl) |
| 48 | 20 | CH$_2$CH=CH | 0 | CH$_3$ | dimethyl cis, trans-3-(4-carbomethoxy-3-butenyl)-4-(4-ethyl-3-hydroxy-1-decenyl) |
| 49 | 21 | (CH$_2$)$_3$ | 1 | C$_2$H$_5$ | diethyl trans-3-(5-carboethoxypentyl)-4-(3-hydroxy-4-methyl-1-heptenyl) |
| 50 | 22 | CH=CHCH$_2$ | 2 | CH$_3$ | dimethyl cis, trans-3-(6-carbomethoxy-2-hexenyl)-4-(3-hydroxy-4-methyl-1-nonenyl) |
| 51 | 23 | CH$_2$CH=CH | 1 | C$_2$H$_5$ | diethyl cis, trans-3-(5-carboethoxy-3-pentenyl)-4-(4-ethyl-3-hydroxy-1-octenyl) |
| 52 | 24 | (CH$_2$)$_3$ | 0 | CH$_3$ | dimethyl trans-3-(4-carbomethoxybutyl)-4-(4-ethyl-3-hydroxy-1-decenyl) |
| 53 | 25 | CH=CHCH$_2$ | 1 | C$_2$H$_5$ | diethyl cis, trans-3-(5-carboethoxy-2-pentenyl)-4-(3-hydroxy-4-propyl-1-heptenyl) |
| 54 | 26 | CH$_2$CH=CH | 2 | CH$_3$ | dimethyl cis, trans-3-(6-carbomethoxy-3-hexenyl)-4-(3-hydroxy-4-propyl-1-nonenyl) |
| 55 | 27 | (CH$_2$)$_3$ | 1 | n-C$_3$H$_7$ | dipropyl trans-3-(5-carbopropoxypentyl)-4-(3-hydroxy-4,4-dimethyl-1-decenyl) |
| 56 | 28 | CH=CHCH$_2$ | 0 | n-C$_3$H$_7$ | dipropyl cis, trans-3-(4-carbopropoxy-2-butenyl)-4-(4-ethyl-(3-hydroxy-4-methyl-1-decenyl) |
| 57 | 29 | CH$_2$CH=CH | 1 | CH$_3$ | dimethyl cis, trans-3-(5-carbomethoxy-3-pentenyl)-4-(3-hydroxy-(4-methyl-4-propyl-1-heptenyl) |
| 58 | 30 | (CH$_2$)$_3$ | 2 | C$_2$H$_5$ | diethyl trans-3-(6-carboethoxyhexyl)-4-(3-hydroxy-4,4-dipropyl-1-nonenyl) |
| 59 | 32 | (CH$_2$)$_3$ | 2 | CH$_3$ | dimethyl trans-3-(6-carbomethoxyhexyl)-4-(3-hydroxy-3-methyl-1-heptenyl) |
| 60 | 33 | CH=CHCH$_2$ | 1 | C$_2$H$_5$ | diethyl cis, trans-3-(5-carboethoxy-2-pentenyl)-4-(3-ethyl-3-hydroxy-1-nonenyl) |
| 61 | 34 | CH$_2$CH=CH | 0 | CH$_3$ | dimethyl cis, trans-3-(4-carbomethoxy-3-butenyl)-4-(3-hydroxy-3-propyl-1-decenyl) |
| 62 | 35 | (CH$_2$)$_3$ | 1 | C$_2$H$_5$ | diethyl trans-3-(5-carboethoxypentyl)-4-(3-hydroxy-3,4-dimethyl-1-heptenyl) |
| 63 | 36 | CH=CHCH$_2$ | 2 | CH$_3$ | dimethyl cis, trans-3-(6-carbomethoxy-2-hexenyl)-4-(3-ethyl-3-hydroxy-4-methyl-1-nonenyl) |
| 64 | 37 | CH$_2$CH=CH | 1 | C$_2$H$_5$ | diethyl cis, trans-3-(5-carboethoxy-3- |

TABLE III-continued

| EX. | NO. OF EXAMPLE IN WHICH STARTING MATERIAL OF FORMULA 4 IS DESCRIBED | STARTING MATERIAL OF FORMULA 5 | | | PRODUCT: (PREFIX LISTED BELOW)-2-OXO-1,3-CYCLO-PENTANEDICARBOXYLATE |
|---|---|---|---|---|---|
| | | Z | m | $R^1$ and $R^3$ | |
| | | | | | pentenyl)-4-(4-ethyl-3-hydroxy-3-propyl-1-octenyl) |
| 65 | 38 | $(CH_2)_3$ | 0 | $CH_3$ | dimethyl trans-3-(4-carbomethoxybutyl)-4-(4-ethyl-3-hydroxy-3-methyl-1-decenyl) |
| 66 | 39 | $CH=CHCH_2$ | 1 | $C_2H_5$ | diethyl cis, trans-3-(5-carboethoxy-2-pentenyl)-4-(3-ethyl-3-hydroxy-4-propyl-1-heptenyl) |
| 67 | 40 | $CH_2CH=CH$ | 2 | $CH_3$ | dimethyl cis, trans-3-(6-carbomethoxy-3-hexenyl)-4-(3-hydroxy-3,4-dipropyl-1-nonenyl) |

EXAMPLE 68 trans, cis-7-[2-(3-Hydroxy-3-methyl-1-octenyl)-5-oxocyclopentyl]-5-heptenoic Acid ($l$, $m=2$, $n=3$, X and Y = O, Z = CH=CHCH$_2$, $R^1$, $R^3$ and $R^4$ = H and $R^2$ = CH$_3$)

The cyclopentanonetriester of formula 6, diethyl cis,trans-3-(6-carboethoxy-2-hexenyl)-4-(3-hydroxy-3-methyl-1-octenyl)-2-oxo-1,3-cyclopentanedicarboxylate (11.2 g), described in Example 45, is heated to reflux for 1 hr. in a solution of sodium hydroxide (13.4 g) in 80 ml of water and 110 ml of methanol. The mixture is cooled, adjusted to pH 5 with 2N HCl, diluted with saturated sodium chloride solution and extracted with ether. The ether extract is dried (Na$_2$SO$_4$) and concentrated. Chromatography on silica gel yields the title compound $\nu_{max}^{CHCl_3}$ 3580, 1740, 1720 cm$^{-1}$, nmr (CDCl$_3$) δ 0.88 (t, J = 5, 3H), 1.28 (s, 3H), 5.3–5.75 (m, 4H), 6.3 (2xs, 2H).

By following the procedure of Example 68 and using the appropriate cyclopentanonetriester of formula 6, for example those described in Examples 45 to 67, then other compounds of formula 1 in which X and Y together represent oxo and $R^1$ is hydrogen are obtained.

For example, the use of the cyclopentanonetriester of formula 6, diethyl trans-3-(6-carboethoxyhexanyl)-4-(3-hydroxy-3-methyl-1-octenyl)-2-oxo-1,3-cyclopentanedicarboxylate, described in Example 45, in the procedure of Example 68, gives trans-7-[2-(3-hydroxy-3-methyl-1-octenyl)-5-oxocyclopentyl]-heptanoic acid, nmr (CDCl$_3$) δ 0.88 (t, 3H), 5.52 (m, 2H), 6.6 (broad singlet, 2H).

Likewise, the use of diethyl cis, trans-3-(6-carboethoxy-2-hexenyl)-4-(3-hydroxy-4-methyl-1-octenyl)-2-oxo-1,3-cyclopentanedicarboxylate, described in Example 45, gives trans, cis-7-[2-(3-hydroxy-4-methyl-1-octenyl)-5-oxocyclopentyl]-5-heptenoic acid, $\gamma_{max}^{film}$ 3450, 1725, 1710 cm$^{-1}$.

Likewise, the use of diethyl cis, trans-3-(6-carboethoxy-3-hexenyl)-4-(3-hydroxy-3-methyl-1-octenyl)-2-oxo-1,3-cyclopentanedicarboxylate, described in Example 45, gives trans, cis-7-[2-(3-hydroxy-3-methyl-1-octenyl)-5-oxocyclopentyl]-4-heptenoic acid, $\gamma_{max}^{film}$ 3620, 3000, 1740, 1720 cm$^{-1}$, nmr (CDCl$_3$) δ 0.89 (t, J = 5, 3H), 2.4 (4H), 5.4 (m, 2H), 5.65 (m, 2H), 5.9 (broad singlet, 2H).

Likewise, the use of dimethyl cis, trans-3-(6-carbomethoxy-2-hexenyl)-4-(3-hydroxy-4,4-dimethyl-1-octenyl)-2-oxo-1,3-cyclopentanedicarboxylate, described in Example 44, gives trans, cis-7-[2-(3-hydroxy-4,4-dimethyl-1-octenyl)-5-oxocyclopentyl]-5-heptenoic acid, $\gamma_{max}^{film}$ 3400–3000, 1730, 1710 cm$^{-1}$, nmr (CDCl$_3$) δ 0.85 (m, 9H), 3.9 (m, 1H), 5.42 (m, 2H), 5.68 (m, 2H), 6.75 (broad s, 2H).

Further examples of such compounds of formula 1 are listed in Table IV together with the requisite cyclopentanonetriesters starting material, the latter compound being noted by the example describing its preparation.

TABLE IV

| EXAMPLE | NO. OF EXAMPLE IN WHICH CYCLOPENTANONETRIESTER OF FORMULA 4 IS PREPARED | PRODUCT: |
|---|---|---|
| 69 | 46 | trans-7-[2-(4-ethyl-3-hydroxy-1-heptenyl)-5-oxocyclopentyl]-heptanoic acid |
| 70 | 47 | trans, cis-6-[2-(3-hydroxy-4-propyl-1-nonenyl)-5-oxocyclopentyl]-4-hexenoic acid |
| 71 | 48 | trans, cis-5-[2-(4-ethyl-3-hydroxy-1-decenyl)-5-oxocyclopentyl]-2-pentenoic acid |
| 72 | 49 | trans-6-[2-(3-hydroxy-4-methyl-1-heptenyl)-5-oxocyclopentyl]-hexanoic acid |
| 73 | 50 | trans, cis-7-[2-(3-hydroxy-4-methyl-1-nonenyl)-5-oxocyclopentyl]-5-heptenoic acid |
| 74 | 51 | trans, cis-6-[2-(4-ethyl-3-hydroxy-1-octenyl)-5-oxocyclopentyl]-3-hexenoic acid |

TABLE IV-continued

| EXAMPLE | NO. OF EXAMPLE IN WHICH CYCLOPENTANONETRIESTER OF FORMULA 4 IS PREPARED | PRODUCT: |
|---|---|---|
| 75 | 52 | trans-5-[2-(4-ethyl-3-hydroxy-l-decenyl)-5-oxocyclopentyl]-pentanoic acid |
| 76 | 53 | trans, cis-6-[2-(3-hydroxy-propyl-l-heptenyl)-5-oxocyclopentyl]-4-hexenoic acid |
| 77 | 54 | trans, cis-7-[2-(3-hydroxy-4-propyl-l-nonenyl)-5-oxocyclopentyl]-4-heptenoic acid |
| 78 | 55 | trans-6-[2-(4,4-dimethyl-3-hydroxy-l-decenyl)-5-oxocyclopentyl]hexanoic acid |
| 79 | 56 | trans, cis-5-[2-(4-ethyl-4-methyl-3-hydroxy-l-decenyl)-5-oxocyclopentyl]-3-pentenoic acid |
| 80 | 57 | trans, cis-6-[2-(4-methyl-3-hydroxy-4-propyl-l-heptenyl)-5-oxocyclopentyl]-3-hexenoic acid |
| 81 | 58 | trans-7-[2-(3-hydroxy-4,4-dipropyl-l-nonenyl)-5-oxocyclopentyl]-heptanoic acid |
| 82 | 59 | trans-7-[2-(3-hydroxy-3-methyl-l-heptenyl)-5-oxocyclopentyl]-heptanoic acid |
| 83 | 60 | trans, cis-6-[2-(3-ethyl-3-hydroxy-l-nonenyl)-5-oxocyclopentyl]-4-hexenoic acid |
| 84 | 61 | trans, cis-5-[2-(3-hydroxy-3-propyl-l-decenyl)-5-oxocyclopentyl]-2-pentenoic acid |
| 85 | 62 | trans-6-[2-(3-hydroxy-3,4-dimethyl-l-heptenyl)-5-oxocyclopentyl]-hexanoic acid |
| 86 | 63 | trans,cis-7-[2-(3-ethyl-3-hydroxy-4-methyl-l-nonenyl)-5-oxocyclopentyl]-5-heptenoic acid |
| 87 | 64 | trans,cis-6-[2-(4-ethyl-3-hydroxy-3-propyl-l-octenyl)-5-oxocyclopentyl]-3-hexenoic acid |
| 88 | 65 | trans-5-[2-(4-ethyl-3-hydroxy-3-methyl-l-decenyl)-5-oxocyclopentyl]pentanoic acid |
| 89 | 66 | trans,cis-6-[2-(3-ethyl-3-hydroxy-4-propyl-l-heptenyl)-5-oxocyclopentyl]-4-hexenoic acid |
| 90 | 67 | trans,cis-7-[2-(3-hydroxy-3,4-dipropyl-l-nonenyl)-5-oxocyclopentyl]-4-heptenoic acid |

EXAMPLE 91

Methyl trans, cis-7-[2-(3-hydroxy-4,4-dimethyl-1-octenyl)-5-oxocyclopentyl]-5-heptenoate (1; $m=2, n=3$, X and Y = O, Z = CH=CHCH$_2$, $R^1$, $R^3$ and $R^4$ = CH$_3$ and $R^2$ = H)

The compound of formula 1, trans,cis-7-[2-(3-hydroxy-4,4-dimethyl-1-octenyl)-5-oxocyclopentyl]-5-heptenoic acid (11.1 g), described in Example 68, is dissolved in 44 ml of absolute methanol containing 2% perchloric acid. The solution is kept at room temperature for 30 min. Thereafter the mixture is rendered neutral with 10%·Na$_2$CO$_3$ and concentrated. The residue is diluted with water and shaken with ether. The ether layer is washed with water, dried (MgSO$_4$) and concentrated to yield the title compound, $\gamma_{max}^{film}$ 3600–3400, 1730, 1710 cm$^{-1}$.

The latter compound is a mixture of epimers with respect to the asymmetric carbon to which the hydroxy group is attached, each epimer being a racemate consisting of a d l pair of stereochemical isomers. By subjecting the preceding product to chromatography on silica gel using ethyl acetate-benzene (1:4) as eluant, the product is separated into its two epimeric forms which are arbitrarily designated Isomer A (least polar isomer) and Isomer B (most polar isomer); the polarity being determined by the order in which these epimers are eluted.

Isomer A: $\gamma_{max}^{film}$ 3470, 1730 cm$^{-1}$, nmr (CDCl$_3$) δ 0.85 (9H), 3.68 (s, 3H), 3.82 (m, 1H), 5.4–5.7 (m, 4H), Rf = 0.88 on thin layer plates of silica gel when using ethyl acetatebenzene (2:3) as the mobile phase.

Isomer B: $\gamma_{max}^{film}$ 3470, 1730 cm$^{-1}$, nmr (CDCl$_3$) δ 3.67 (s, 3H), 3.82 (m, 1H), 5.41 (m, 2H), 5.66 (m, 2H), Rf = 0.69 on thin layer plates of silica gel when using ethyl acetate-benzene (2:3) as the mobile phase.

In the same manner but using the appropriate choice of the compound of formula 1 and lower alkanol, other corresponding esters of formula 1 ($R^1$ = lower alkyl) are prepared; for example, the corresponding lower alkyl esters of the products of Table IV. More specifically exemplified, the choice of trans-7-[2-(3-hydroxy-3-methyl-1-octenyl)-5-oxocyclopentyl]heptanoic acid, described in Example 68, as the compound of formula 1 and methanol as the lower alkanol in the procedure of this example give methyl trans-7-[2-(3-hydroxy-3-methyl-1-octenyl)-5-oxocyclopentyl]heptanoate, $\gamma_{max}^{film}$ 3475, 1730 cm$^{-1}$, nmr (CDCl$_3$) δ 0.89 (t, 3H), 3.64 (s, 3H), 5.61 (m, 2H).

Likewise, the choice of trans, cis-7-[2-(3-hydroxy-3-methyl-1-octenyl)-5-oxocyclopentyl]-5-heptenoic acid described in Example 68, and methanol, gives methyl trans, cis-7-[2-(3-hydroxy-3-methyl-1-octenyl)-5- oxocyclopentyl]-5-heptenoate, $\gamma_{max}^{film}$ 1738, 1730 cm$^{-1}$.

Likewise, the choice of trans, cis-7-[2-(3-hydroxy-4-methyl-1-octenyl)-5-oxocyclopentyl]-5-heptenoic acid and methanol gives methyl trans, cis-7-[2-(3-hydroxy-4-methyl-1-octenyl)-5-oxocyclopentyl]-5-heptenoate, $\gamma_{max}^{film}$ 1732 cm$^{-1}$, nmr (CDCl$_3$) δ 3.65 (s, 3H), 5.25–5.75 (m, 4H).

Likewise, the choice of trans, cis-7-[2-(3-hydroxy-3-methyl-1-octenyl)-5-oxocyclopentyl]-4-heptenoic acid and ethanol gives ethyl trans, cis-7-[2-(3-hydroxy-3-methyl-1-octenyl)-5-oxocyclopentyl]-4-heptenoate, $\gamma_{max}^{film}$ 1740, 1732 cm$^{-1}$.

EXAMPLE 92

Methyl trans, cis-7-[2-hydroxy-5-(3-hydroxy-4,4-dimethyl-1-octenyl)cyclopentyl]-5-heptenoate (1; $m = 2, n = 3$, X = OH, Y = H, Z = CH=CHCH$_2$, R$^1$, R$^3$ and R$^4$ = CH$_3$ and R$^2$ = H)

A solution of borane (11 ml of 1M soln.) in THF is added to a solution of pinene (2.99 g) in dry diglyme (8.0 ml) at −10° C (bath temp.) in a N$_2$ atmosphere. The mixture is stirred for 10 min. then cooled to −78° C. To this mixture tert-butyl lithium (5.5 ml, 2.1 molar in pentane) is added slowly, maintaining the temp. of the reaction at −78° C. After stirring for 10 min., a solution of methyl trans, cis-7-[2-(3-hydroxy-4,4-dimethyl-1-octenyl)-5-oxocyclopentyl]-5-heptenoate, Isomer B (1.37 g), described in Example 91, in diglyme-THF (8.8 ml, 1:0.7) is added to the mixture. The temperature is maintained at −78° C for 1 hour. The cooling bath is removed and, the reaction is quenched by adding 10% sodium hydroxide solution (8 ml) and 30% hydrogen peroxide solution (8 ml). The mixture is then diluted with water and extracted with ether. The ether extract is washed with water and 3% HCl soln. to render it neutral, dried (MgSO$_4$) and concentrated to yield the title compound (Isomer B) $\gamma_{max}^{film}$ 3600–3440, 1730–1720 cm$^{-1}$. This product is a mixture of epimers with the respect to the asymmetric carbon of the cyclopentane ring to which the hydroxy group is attached, each epimer being a racemate consisting of a d l pair of stereochemical isomers. The product is separated into these two epimers by subjecting it to chromatography on silica gel (135 g) using ethyl acetate-benzene (1:4) as eluant. In this manner the product is separated into a first epimer (less polar) and a second epimer (more polar):

Less polar epimer $\gamma_{max}^{film}$ 3400, 1730–1720 cm$^{-1}$, nmr (CDCl$_3$) δ 0.88 (m, 9H), 3.68 (s, 3H), 3.79 (m, 1H), 4.2m, 1H), 5.5 (m, 4H), Rf = 0.52 on thin layer plates of silica gel when using ethyl acetate-benzene (2:3) as the mobile phase.

More polar epimer $\gamma_{max}^{film}$ 3400, 1726 cm$^{-1}$, nmr (CDCl$_3$) δ 0.88 (m, 9H), 3.67–3.95 (m, 5H), 5.52 (m, 4H), Rf = 0.41 on thin layer plates of silica gel when using ethyl acetate-benzene (2:3) as the mobile phase.

Comparative data with the nmr spectra of known hydroxyprostaglandin derivatives, for example see J. F. Bagli and T. Bogri, Tetrahedron Letters, 1639 (1969), and the order of elution of known hydroxyprostaglandin derivatives, see for example J. E. Pike, et al., J. Org. Chem., 34, 3552 (1969), indicate that the C-2 hydroxy group and the C-1 acid side chain of the above less polar epimer have a cis relationship whereas the C-2-hydroxy group and the C-1 acid side chain of the above more polar epimer have a trans relationship.

In other words the data indicate that the less polar epimer is racemic methyl trans, cis-7-[2α-hydroxy-5-(3-hydroxy-4,4-dimethyl-1-octenyl)cyclopentyl]-5-heptenoate and the more polar isomer is racemic methyl trans, cis-7-[2β-hydroxy-5-(3-hydroxy-4,4-dimethyl-1-octenyl)cyclopentyl]-5-heptenoate.

In the same manner but replacing methyl trans, cis-7-[2-(3-hydroxy-4,4-dimethyl-1-octenyl)-5-oxocyclopentyl]-5-heptenoate, Isomer B, with the corresponding Isomer A, described in Example 91, Isomer A of the title compound is obtained, $\gamma_{max}^{film}$ 3600, 1732–1720 cm$^{-1}$, which in turn can be separated into its less polar and more polar epimer. The less polar epimer of Isomer A, racemic methyl trans, cis-7-[2α-hydroxy-5-(3-hydroxy-4,4-dimethyl-1-octenyl)cyclopentyl]-5-heptenoate [nmr (CDCl$_3$) δ 4.2] has a Rf = 0.68 on thin layer plates of silica gel using ethyl acetate-benzene (2:3) as the mobile phase and the more polar epimer of Isomer A, racemic methyl trans, cis-7-[2β-hydroxy-5-(3-hydroxy-4,4-dimethyl-1-octenyl)cyclopentyl]-5-heptanoate [nmr (CDCl$_3$) δ 3.7–3.9] has a Rf = 0.47 on silica gel plates using ethyl acetate-benzene (2:3) as the mobile phase.

In the same manner but using the appropriate oxo compound of formula 1, other corresponding hydroxy compounds of formula 1 in which X is hydroxy, Y is hydrogen and R$^1$ is lower alkyl are prepared; for example, the corresponding lower alkyl esters of the hydroxy compounds of the products of Table IV.

More specifically the choice of the oxo compound of formula 1, methyl trans-7-[2-(3-hydroxy-3-methyl-1-octenyl)-5-oxocyclopentyl]heptanoate, described in Example 91, in the procedure of this example gives methyl trans-7-[2-hydroxy-5-(3-hydroxy-3-methyl-1-octenyl)cyclopentyl]heptanoate, $\gamma_{max}^{film}$ 3410, 1730 cm$^{-1}$.

Likewise, the choice of methyl trans, cis-7-[2-(3-hydroxy-3-methyl-1-octenyl)-5-oxocyclopentyl]-5-heptenoate, gives methyl trans, cis-7-[2-hydroxy-5-(3-hydroxy-3-methyl-1-octenyl)cyclopentyl]-5-heptenoate, $\gamma_{max}^{film}$ 3600, 1735 cm$^{-1}$, which can be separated into its less polar and more polar epimer. The less polar epimer, racemic methyl trans, cis-7-[2α-hydroxy-5-(3-hydroxy-3-methyl-1-octenyl)cyclopentyl]-5-heptenoate [nmr (CDCl$_3$) δ 4.28] has a Rf = 0.36 on silica gel thin layer plates using ethyl acetate-benzene (3:7) as the mobile phase and the more polar epimer racemic methyl trans,cis-7-[2β-hydroxy-5-(3-hydroxy-3-methyl-1-octenyl)cyclopentyl]-5-heptenoate [nmr (CDCl$_3$) δ 3.90] has a Rf = 0.28 on silica gel thin layer plates using the same mobile phase.

Likewise, the choice of methyl trans,cis-7-[2-(3-hydroxy-4-methyl-1-octenyl)-5-oxocyclopentyl]-5-heptenoate, described in Example 91, gives methyl trans, cis-7-[2-hydroxy-5-(3-hydroxy-4-methyl-1-octenyl)cyclopentyl]-5-heptenoate, $\gamma_{max}^{film}$ 3600, 1732 cm$^{-1}$.

Likewise, the choice of methyl trans, cis-7-[2-(3-hydroxy-3-methyl-1-octenyl)-5-oxocyclopentyl]-4-heptenoate, described in Example 91, gives methyl trans, cis-7-[2-hydroxy-5-(3-hydroxy-3-methyl-1-octenyl)cyclopentyl]-4-heptenoate, $\gamma_{max}^{film}$ 3600, 1730 cm$^{-1}$, which can be separated into its less polar and more polar epimer. The less polar epimer, racemic methyl trans, cis-7-[2α-hydroxy-5-(3-hydroxy-3-methyl-1-octenyl)cyclopentyl]-4-heptenoate has nmr (CDCl$_3$) δ 2.38 (4H), 4.28 (1H), 5.5 (4H) and the more polar epimer racemic methyl trans, cis-7-[2β-hydroxy-5-(3-hydroxy-3-methyl-1-octenyl)cyclopentyl]-4-heptenoate has nmr (CDCl$_3$) δ 2.4 (4H), 3.98 (1H), 5.57 (4H).

EXAMPLE 93 trans, cis-7-[2-Hydroxy-5-(3-hydroxy-4,4-dimethyl-1-octenyl)cyclopentyl]-5-heptenoic Acid (1), 1; $m = 2$, $n = 3$, $X = OH$, $Y = H$, $Z = CH=CHCH_2$, $R^1$ and $R^2 = H$ and $R^3$ and $R^4 = CH_3$)

To a solution of trans, cis-7-[2-hydroxy-5-(3-hydroxy-4,4-dimethyl-1-octenyl)cyclopentyl]-5heptenoate (0.536 g, Isomer B less polar epimer), described in Example 92, in methanol (5 ml) is added a solution of sodium hydroxide (10%, 1.32 ml). The mixture is stirred for 18 hr. The solvent is removed under reduced pressure and the residue taken up in water and extracted with ether. The aqueous liquor is then rendered acidic with HCl (10%, 1.32 ml). The precipitate is taken up with ether. The ether extract is washed with water, dried (Na$_2$SO$_4$) and the solvent is removed to yield the title compound, Isomer B less polar epimer, nmr (CDCl$_3$) δ 0.84 (m, 9H), 3.80 (m, 1H), 4.23 (m, 1H), 5.27 (broad, 3H), 5.5 (m, 4H), (i.e., racemic trans, cis-7-[2α-hydroxy-4,4-dimethyl-1-octenyl)cyclopentyl]-5-heptenoic acid).

In the same manner the Isomer B-more polar epimer, Isomer A-more polar epimer and the Isomer A-less polar epimer of methyl trans, cis-7-[2-hydroxy-5-(3-hydroxy-4,4-dimethyl-1-octenyl)cyclopentyl]-5-heptanoate, described in Example 92, are converted to the respective Isomer B-more polar epimer, Isomer A-more polar epimer and the Isomer A-less polar Isomer of the title compound.

In the same manner but using the appropriate ester compound of formula 1 in which X is hydroxy, Y is hydrogen and R$^1$ is hydrogen are prepared; for example the corresponding hydroxy compounds of the products of Table IV.

More specifically exemplified, the choice of methyl trans-7-[2-hydroxy-5-(3-hydroxy-3-methyl-1-octenyl)-cyclopentyl]heptanoate, described in Example 92, in the procedure of this example gives trans-7-[2-hydroxy-5-(3-hydroxy-3-methyl-1-octenyl)cyclopentyl]heptanoic acid, nmr (CDCl$_3$) δ 0.9 (t, 3H), 4.0–4.3 (m, 1H), 5.5 (m, 2H).

Likewise, the choice of methyl trans-7-[2-hydroxy-5-(3-hydroxy-3-methyl-1-octenyl)cyclopentyl]heptanoate, more polar or less polar epimer, described in Example 94, gives the respective more polar [nmr (CDCl$_3$) δ 3.95] and less polar epimer [nmr (CDCl$_3$) δ 4.25] of trans-7-[2-hydroxy-5-(3-hydroxy-3-methyl-1-octenyl)cyclopentyl]heptanoic acid. In other words trans-7-[2β-hydroxy- and trans-7-[2α-hydroxy-5-(3-hydroxy-3-methyl-1-octenyl)cyclopentyl]heptanoic acid are obtained, respectively (see Example 92 for the significance of the nmr peaks).

Likewise, the choice of methyl trans, cis-7-[2-hydroxy-5-(3-hydroxy-3-methyl-1-octenyl)cyclopentyl]-5-heptenoate, described in Example 92, gives trans, cis-7-[2-hydroxy-5-(3-hydroxy-3-methyl-1-octenyl)cyclopentyl]-5-heptenoic acid, $\gamma_{max}^{film}$ 3610, 3450, 1718 cm$^{-1}$.

Likewise, the choice of methyl trans, cis-7-[2-hydroxy-5-(3-hydroxy-3-methyl-1-octenyl)cyclopentyl]-5-heptenoate, more polar and less polar epimer, described in Example 92, gives the respective more polar [nmr (CDCl$_3$) δ 3.95 (1H), 5.55 (2H)] and less polar epimer [nmr (CDCl$_3$) δ 4.27 (1H), 5.5 (2H)], namely trans, cis-7-[2β-hydroxy-5-(3-hydroxy-3-methyl-1-octenyl)cyclopentyl]-5-heptenoic acid and trans, cis-7-[2α-hydroxy-5-(3-hydroxy-3-methyl-1-octenyl)-cyclopentyl]-5-heptenoic acid respectively.

Likewise, the choice of methyl trans, cis-7-[2-hydroxy-5-(3-hydroxy-4-methyl-1-octenyl)cyclopentyl]-5-heptenoate, described in Example 92, gives trans, cis-7-[2-hydroxy-5-(3-hydroxy-4-methyl-1-octenyl)cyclopentyl]-5-heptenoic acid.

Likewise, the choice of the less and more polar epimer of methyl trans, cis-7-[2-hydroxy-5-(3-hydroxy-3-methyl-1-octenyl)cyclopentyl]-4-heptenoate, described in Example 92, gives the respective less and more polar epimer of trans, cis-7-[2-hydroxy-5-(3-hydroxy-3-methyl-1-octenyl)cyclopentyl]-4-heptenoic acid. In other words, trans, cis-7-[2α-hydroxy-5-(3-hydroxy-3-methyl-1-octenyl)cyclopentyl]-4-heptenoic acid [nmr (CDCl$_3$) δ 4.28] and trans, cis-7-[2β-hydroxy-5-(3-hydroxy-3-methyl-1-octenyl)cyclopentyl]-4-heptenoic acid [nmr (CDCl$_3$) δ 3.98] are obtained, respectively.

EXAMPLE 94

Methyl trans-7-[2-hydroxy-5-(3-hydroxy-3-methyl-1-octenyl)-cyclopentyl]heptanoate (1; $m = 2$, $n = 3$, $X = OH$, $Y = H$, $Z = (CH_2)_3$, $R^1$ and $R^2 = CH_3$, $R^3$ and $R^4 = H$)

The compound of formula 3, methyl trans-7-[2-(3-oxo-1-octenyl)-5-(trimethylsilyloxy)cyclopentyl]heptanoate [3; R$^3$ and R$^4$ = H, $n = 3$ and L = radical B wherein Z = (CH$_2$)$_3$, $m = 2$, R$^1$ = CH$_3$ and R$^6$ = Si(CH$_3$)$_3$], $\gamma_{max}^{film}$ 1737, 1678, 1625 cm$^{-1}$, nmr (CDCl$_3$) δ 0.12 (9H), 0.9 (3H), 3.68 (3H), 4.24 (1H), 6.5 (2H), is prepared by treating the precusor to the aldehyde of formula L—CHO in which L is the radical B, '-(6-carboxylhexyl)cyclopentan-1-ol-3-al, prepared as described in copending application Ser. No. 259,896, noted above, with 1.2 equivalents of both trimethylchlorosilane and hexamethyldisilazane in THF at 60° C for 1 hour, followed by treatment of the resulting aldehyde of formula L—CHO with dimethyl 2-oxoheptylphosphonate according to the procedure of Example 2. Alternatively, the last named compound of formula 3 is prepared by treating methyl trans-7-[2-(3-oxo-1-octenyl)-5-hydroxycyclopentyl]heptanoate, described in U.S. Pat. No. 3,455,992, issued July 15, 1969, with trimethylchlorosilane and hexamethyldisilazane in the same manner.

The said last named compound of formula 3 (18.76 g) in dry ether (80 ml) is cooled to −5° C and added to a solution of methyl magnesium iodide (prepared from 1.23 g of magnesium turnings and 7.63 g of methyl iodide) in 100 ml of dry ether at −5° C. After 15 min. of stirring the reaction mixture is quenched with 10 ml of saturated ammonium chloride (10 ml) while maintaining the temperature at −5° to 0° C. The mixture is diluted with ether, washed with water, dried (Na$_2$SO$_4$) and concentrated to yield methyl trans-7-[2-(3-hydroxy-3-methyl-1-octenyl)-5-(trimethylsilyloxy)cyclopentyl]heptanoate [4; R$^2$ = CH$_3$, R$^3$, R$^4$ and R$^7$ = H, $n = 3$ and L = radical B wherein Z = (CH$_2$)$_3$, $m = 2$, R$^1$ = CH$_3$ and R$^6$ = Si(CH$_3$)$_3$], $\gamma_{max}^{film}$ 3400, 1740, 1712, 1250, 848 cm$^{-1}$, nmr (CDCl$_3$) δ 0.1 (9H), 0.92 (3H), 1.3 (s, 3H), 3.7 (s, 3H), 5.5 (m, 2H)

The latter compound (18.85 g) in THF (16.8 ml), water (47.2 ml) and acetic acid (25 ml) is stirred at room temperature for 2 hr. The mixture is cooled in an ice bath and rendered neutral by the careful addition of sodium carbonate (20 g). The mixture is extracted with ether. The ether extract is washed with water, dried (Na$_2$SO$_4$) and concentrated to yield the title compound, $\gamma_{max}^{film}$ 3410, 1730 cm$^{-1}$, identical to the product of the same name described in Example 92. This product is a mixture of epimers with respect to the asymmetric carbon of the cyclopentane ring to which the hydroxy group is attached. In the same manner as for the the title compound of Example 92, the present product is separated into a first epimer (less polar) and second epimer (more polar):

Less polar epimer: $\gamma_{max}^{film}$ 3430, 1730 cm$^{-1}$, nmr (CDCl$_3$) δ 0.90 (t, 3H), 3.68 (s, 3H), 4.2 (m, 1H), 5.5 (m, 2H), More polar epimer: $\gamma_{max}^{film}$ 3350, 1730 cm$^{-1}$, nmr (CDCl$_3$) δ 0.88 (t, 3H), 3.68 (s, 3H), 3.90 (m, 1H), 5.55 (m, 2H).

As discussed in Example 92, comparative data with the spectra of known hydroxyprostaglandin derivatives indicate that the preceding less polar epimer is a racemic mixture of methyl trans-7-[2α-hydroxy-5-(3-hydroxy-3-methyl-1-octenyl)cyclopentyl]heptanoate and that the preceding more polar isomer is racemic mixture of methyl trans-7-[2β-hydroxy-5-(3-hydroxy-3-methyl-1-octenyl)cyclopentyl]heptanoate. The respective Rf's of these two racemic mixtures are 0.44 and 0.29 on thin layer plates of silica gel when using ethyl acetate-benzene (1:4) as the mobile phase.

In the same manner but replacing methyl magnesium iodide with an equivalent amount of ethyl magnesium bromide or propyl magnesium bromide, methyl trans-7-[2-(3-hydroxy-3-propyl-1-octenyl)-5-hydroxycyclopentyl]-5-heptenoate and methyl trans-7-[2-(3-hydroxy-3-propyl-1-octenyl)-5-hydroxycyclopentyl]-5-heptenoate are obtained, respectively.

In the same manner but replacing the compound of formula 3, methyl trans-7-[2-(3-oxo-1-octenyl)-5-(trimethylsilyloxy)cyclopentyl]-5-heptenoate, with the appropriate compound of formula 3 in which L is radical B, then other compound of formula 1 in which $m, n$, Z, R$^2$, R$^3$ and R$^4$ are as defined in the first instance X is hydroxy, Y is hydrogen and R$^1$ is lower alkyl are obtained; for example, the products of formula 1 in which R$^2$ is methyl described in Example 92. More specifically exemplified, replacement of the compound of formula 3 with methyl trans, cis-7-[2-(3-oxo-1-octenyl)-5-[(tetrahydropyran-2-yl)oxy]cyclopentyl]-5-heptenoate gives methyl trans,cis-7-[2-hydroxy-5-(3-hydroxy-3-methyl-1-octenyl)cyclopentyl]-5-heptenoate, described in Example 92.

EXAMPLE 95

Methyl trans-7-[2-(3-hydroxy-3-methyl-1-octenyl)-5-oxocyclopentyl]heptanoate (1; $m = 2, n = 3$, X and Y = 0, Z = (CH$_2$)$_3$, R$^1$ and R$^2$ = CH$_3$ and R$^3$ and R$^4$ = H)

To a solution of dry pyridine (5.85 ml) in methylene chloride (135. ml, purified by shaking with H$_2$SO$_4$, and dried over CaO, and distilled) is added chromic acid (4 g) at 15° C. The mixture is stirred for 20 min. To this mixture is added a solution of the compound of formula 1 in which R$^2$ is methyl, methyl trans-7-[2-hydroxy-5-(3-hydroxy-3-methyl-1-octenyl)cyclopentyl]heptanoate, described in Example 92, in methylene chloride (50 ml). The mixture is stirred for 1 hour. The reaction mixture is filtered and the collected slurry on the filter pad is washed with more methylene chloride. The organic phase of the filtrate and washing are combined and washed with water, dried (Na$_2$SO$_4$) and the solvent concentrated, to yield the crude product. Chromatography of the product on a silica gel column affords the title compound, identical to the product of the same name described in Example 91.

In the same manner other compounds of formula 1 in which X is hydroxy, Y is hydrogen and R$^2$ is lower alkyl, for example the other compounds of formula 1 in which R$^2$ is methyl of Example 92, are oxidized to their corresponding compounds of formula 1 in which R$^2$ is lower alkyl, for example methyl.

EXAMPLE 96

Methyl trans, cis-7-[2-(3-hydroxy-4,4-dimethyl-1-octenyl)-5-oxocyclopentyl]-5-heptenoate (1; $m = 2, n = 3$, X and Y = 0, Z = (CH$_2$)$_3$, R$^1$ and R$^2$ = CH$_3$ and R$^3$ and R$^4$ = H).

A mixture of the compound of formula 3 in which L is the radical C, methyl trans-7-[2-(4,4-dimethyl-3-oxo-1-octenyl)-5-oxo-cyclopentyl]-5-heptenoate (2.5 g, $\gamma_{max}^{film}$ 1730–1725, 1667, 1620 cm$^{-1}$), ethylene glycol (360 mg) and p-toluenesulfonic acid (35 mg) in 50 ml of benzene is heated at reflux for 2.5 hr. Thereafter the mixture is extracted with ether. The ether extract is washed with water, dried (MgSO$_4$) and concentrated under reduced pressure. The residue containing methyl trans, cis-7-[2-(ethylenedioxy)-5-(4,4-dimethyl-3-oxo-1-octenyl)cyclopentyl-5-heptenoate, $\gamma_{max}^{film}$ 1730, 1667, 1620 cm$^{-1}$, is taken up in 20 ml of methanol and treated with sodium borohydride (350 mg) in small portions with stirring which is continued for 30 minutes. The solvent is evaporated under reduced pressure, the residue taken up in ether, washed to neutrality with water, dried (MgSO$_4$) and the solvent concentrated under reduced pressure. The residue is chromatographed on silica gel (140 g). Elution with ethyl acetate-benzene (4:1) and concentration of the eluant affords methyl trans,cis-7-[2-(ethylenedioxy)-5-(3-hydroxy-4,4-dimethyl-1-octenyl)cyclopentyl]-5-heptenoate, $\gamma_{max}^{film}$ 3460, 1740, 950 cm$^{-1}$.

The latter compound (50 mg) is dissolved in methanol water (9:1) containing 20 mg of p-toluenesulfonic acid. This mixture is allowed to stand at room temperature overnight. The mixture is diluted with ether and washed with water. The ether extract is dried (MgSO$_4$) and the solvent evaporated under reduced pressure to yield the title compound, identical to the product of the same name described in Example 91.

In the same manner other compounds of formula 1 in which X and Y together are oxo, R$^1$ is lower alkyl and R$^2$ is hydrogen, for example, the corresponding lower alkyl esters of Examples 69 to 81, are obtained by using the appropriate corresponding compound of formula 3 in which L is the radical C.

The requisite compounds of formula 3 in which L is the radical C are prepared by reacting the appropriate aldehyde of formula LCHO in which L is the radical C, prepared by the procedure described in copending U.S. application Ser. No. 259,896, noted above, with the appropriate Wittig reagent of formula (AlkO)$_2$POCH- $_2COR^3R^4(CH_2)_nCH_3$ in which at least one of $R^3$ and $R^4$ is lower alkyl, described above, according to the procedure of Example 2. For example, methyl trans, cis-7-[2-(4,4-dimethyl-3-oxo-1-octenyl)-5-oxocyclopentyl]-5-heptanoate, utilized above, is prepared by treating 2-(6-carboxy-2-hexenyl)cyclopentane-1-on-3-al with the Wittig reagent, dimethyl 3,3-dimethyl-2-oxoheptyl phosphonate, described in Example 1, according to the procedure of Example 3.

EXAMPLE 97

Diethyl trans-2-(3-oxo-1-butenyl)cyclopropane-1,1-dicarboxylate (12; L = radical A in which $R^5 = C_2H_5$ and $R^9 = CH_3$)

A solution of diethyl 2-formylcyclopropane-1,1-dicarboxylate (14 g) in acetone (40 ml) is added slowly (about 5 hr. of addition time) to a boiling mixture of piperidine (3 ml) and acetone (140 ml). After this addition the reaction mixture is heated at reflux for an additional hour. The excess acetone is removed under reduced pressure. The residue is diluted with water and extracted with benzene. The extract is dried ($Na_2SO_4$) and evaporated to dryness. The residue is dissolved in acetonehexane (1:9) and the solution poured through a column of silica gel. The eluate is concentrated to give the title compound $\gamma_{max}^{film}$ 1725, 1670, 1625 cm$^{-1}$, nmr (CDCl$_3$ $\delta$ 1.26 (t, J = 8, 3H), 1.8 (m, 2H), 2.2 (3H), 2.6 (1H), 4.25 (q, 2H), 6.23 and 6.28 (2H).

In the same manner but replacing diethyl 2-formylcyclopropane-1,1-dicarboxylate with dimethyl 2-formylcyclopropane-1,1-dicarboxylate, the corresponding methyl ester of the title compound, dimethyl trans-2-(3-oxo-1-butenyl)cyclopropane-1,1-dicarboxylate is obtained.

Thereafter, by following the procedure of Example 31 but replacing diethyl trans-2-(3-oxo-1-octenyl)cyclopropane-1,1-dicarboxylate and methyl magnesium iodide with equivalent amounts of the title compound and pentyl magnesium bromide, respectively, diethyl trans-2-(3-hydroxy-3-methyl-1-octenyl)cyclopropane-1,1-dicarboxylate, identical to the product of the same name described in Example 31, is obtained. Similarly the use of the title compound or its corresponding methyl ester and the appropriate lower alkyl magnesium halide in which the alkyl portion is $CR^3R^4—(CH_2)_nCH_3$ in which $R^3$ is hydrogen, $R^4$ is hydrogen or lower alkyl and n is as defined hereinbefore gives the corresponding compound of formula 4; for example, the use of the corresponding methyl ester of the title compound and butyl magnesium iodide gives dimethyl trans-2-(3-hydroxy-3-methyl-1-heptenyl)cyclopropane-1,1-dicarboxylate, described in Example 32.

In the same manner but replacing acetone with an equivalent amount of 2-butanone or 2-pentanone, diethyl trans-2-(3-oxo-1-pentenyl)cyclopropane-1,1-dicarboxylate and diethyl trans-2-(3-oxo-1-hexenyl)cyclopropane-1,1-dicarboxylate are obtained, respectively. Thereafter, and likewise, treatment of the appropriate choice of one of the latter two compounds with the appropriate lower alkyl magnesium halide in which the alkyl portion is $CR^3R^4—(CH_2)_nCH_3$ in which $R^3$, $R^4$ and n are as defined in the last instance gives the corresponding compound of formula 4.

EXAMPLE 98

Diethyl trans-2-(3-oxo-1-octenyl)cyclopropane-1,1-dicarboxylate (12; L = radical A in which $R^5 = C_2H_5$ and $R^9 = n—C_5H_{11}$)

Equimolar quantities of the aldehyde of formula 2, diethyl 2-formylcyclopropane-1,1-dicarboxylate, 2-heptanone and piperidine are heated at reflux in benzene (2.6 ml for each gram of aldehyde) for 2–5 hr. The azeotrope is collected giving about one mole of water. The mixture is diluted with fresh benzene. The benzene layer is washed with water, dried ($Na_2SO_4$) and concentrated. The residue is subjected to chromatography [eluent = acetone-hexane (1:4)] to give the title compound identical to the product of the same name described in Example 3.

In the same manner but replacing 2-heptanone with the appropriate methyl ketone of formula $CH_3COR^9$ in which $R^9$ is $CR^3R^4—(CH_2)_nCH_3$ and defined hereinbefore then other corresponding compounds of formula 12 are obtained; for example, such replacement of 2-heptanone with 3-methyl-2-heptanone or 2-nonanone gives diethyl trans-2-(4-methyl-3-oxo-1-octenyl)cyclopropane-1,1-dicarboxylate, described in Example 3, and diethyl trans-2-(3-oxo-1-decenyl)cyclopropane-1,1-dicarboxylate, respectively.

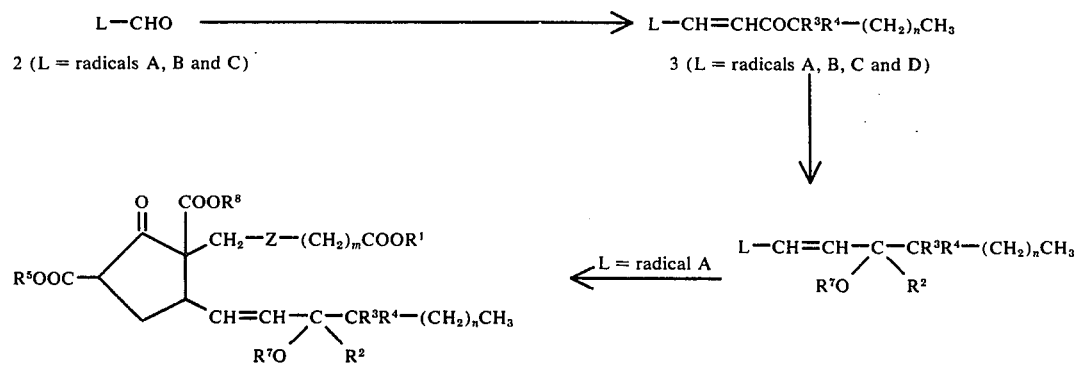

-continued

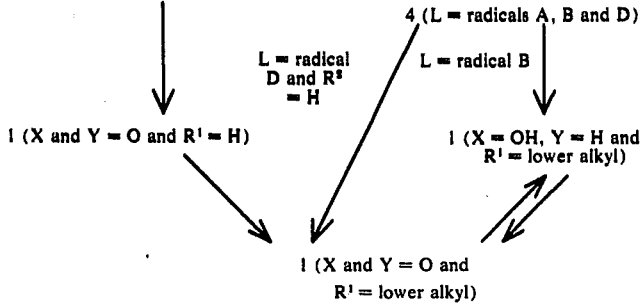

We claim:
1. A compound of the formula

L—CH=CHCOCR³R⁴—(CH₂)ₙCH₃ in which L is the radical

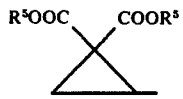

wherein $R^5$ is lower alkyl, $R^3$ and $R^4$ each are hydrogen or lower alkyl with the proviso that at least one of $R^3$ and $R^4$ is lower alkyl, and $n$ is an integer from two to five.

2. Dimethyl and diethyl trans-2-(4,4-dimethyl-3-oxo-1-octenyl)cyclopropane-1,1-dicarboxylate, as claimed in claim 1.

3. Diethyl trans-2-(4-methyl-3-oxo-1-octenyl)cyclopropane-1,1-dicarboxylate, as claimed in claim 1.

4. Diethyl trans-2-(3-oxo-1-butenyl)cyclopropane-1,1-dicarboxylate.

5. A compound of the formula

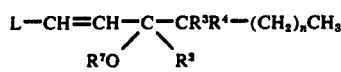     (4)

in which L is the radical

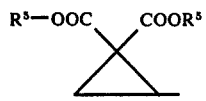

wherein $R^5$ is lower alkyl, $R^2$, $R^3$ and $R^4$ each are hydrogen or lower alkyl with the provisos that at least one of $R^2$, $R^3$ or $R^4$ is hydrogen and at least one of $R^2$, $R^3$ and $R^4$ is lower alkyl, $R^7$ is hydrogen or a radical suitable for protecting a hydroxyl group selected from the class consisting of tetrahydropyran-2-yl, tetramethylsilyl, dimethylisopropylsilyl and tertiarybutyl, and $n$ is an integer from two to five.

6. Diethyl trans-2-(3-hydroxy-4,4-dimethyl-1-octenyl)-cyclopropane-1,1-dicarboxylate, as claimed in claim 5.

7. Diethyl trans-2-(3-hydroxy-4-methyl-1-octenyl)-cyclopropane-1,1-dicarboxylate, as claimed in claim 5.

8. Diethyl trans-2-(3-hydroxy-3-methyl-1-octenyl)-cyclopropane-1,1-dicarboxylate, as claimed in claim 5.

9. Diethyl trans-2-{3-[(tetrahydropyran-2-yl)oxy]-3-methyl-1-octenyl}cyclopropane-1,1-dicarboxylate, as claimed in claim 5.

10. Diethyl trans-2-{3-[(tetrahydropyran-2-yl)oxy]-4-methyl-1-octenyl}cyclopropane-1,1-dicarboxylate, as claimed in claim 5.

* * * * *